(12) United States Patent
Ward et al.

(10) Patent No.: US 6,902,914 B2
(45) Date of Patent: Jun. 7, 2005

(54) RECOMBINANT DNA PROCESSES USING A DNTP MIXTURE CONTAINING MODIFIED NUCLEOTIDES

(75) Inventors: Brian Ward, St. Louis, MO (US); Leanne M. Snyder, St. Louis, MO (US); Chuan Li, St. Louis, MO (US); Keming Song, Ballwin, MO (US); Kristen E. Opper, Collinsville, IL (US); Stephanie Uder, Edwardsville, IL (US); Ron Hernan, St. Louis, MO (US)

(73) Assignee: Sigma-Aldrich, Co., Highland, IL (US)

( * ) Notice: Subject to any disclaimer, the term of this patent is extended or adjusted under 35 U.S.C. 154(b) by 159 days.

(21) Appl. No.: 10/002,292

(22) Filed: Nov. 15, 2001

(65) Prior Publication Data

US 2003/0099956 A1 May 29, 2003

Related U.S. Application Data

(60) Provisional application No. 60/325,612, filed on Sep. 28, 2001.

(51) Int. Cl.[7] .......................... C12P 19/34; C07H 21/04
(52) U.S. Cl. ................... 435/91.1; 435/91.2; 536/26.7; 536/26.8
(58) Field of Search .............................. 536/26.7, 26.8; 435/91.1, 91.2, 810

(56) References Cited

U.S. PATENT DOCUMENTS

| | | | |
|---|---|---|---|
| 4,521,509 A | | 6/1985 | Benkovic et al. |
| 4,532,207 A | | 7/1985 | Brewer et al. |
| 4,569,794 A | | 2/1986 | Smith et al. |
| 4,682,195 A | | 7/1987 | Yilmaz |
| 4,683,195 A | | 7/1987 | Mullis et al. |
| 4,683,202 A | | 7/1987 | Mullis |
| 4,800,159 A | | 1/1989 | Mullis et al. |
| 4,851,341 A | | 7/1989 | Hopp et al. |
| 5,075,227 A | | 12/1991 | Hagen |
| 5,260,427 A | | 11/1993 | Spielvogel et al. |
| 5,284,933 A | | 2/1994 | Dobeli et al. |
| 5,310,663 A | | 5/1994 | Dobeli et al. |
| 5,455,166 A | * | 10/1995 | Walker ...................... 435/91.2 |
| 5,487,993 A | | 1/1996 | Herrnstadt et al. |
| 5,518,900 A | | 5/1996 | Nikiforov et al. |
| 5,518,901 A | | 5/1996 | Murtagh |
| 5,523,221 A | | 6/1996 | Weiner |
| 5,580,759 A | | 12/1996 | Yang et al. |
| 5,594,115 A | | 1/1997 | Sharma |
| 5,595,895 A | | 1/1997 | Miki et al. |
| 5,604,098 A | | 2/1997 | Mead et al. |
| 5,659,027 A | | 8/1997 | Spielvogel et al. |
| 5,683,869 A | | 11/1997 | Shaw et al. |
| 5,688,669 A | | 11/1997 | Murtagh |
| 5,744,306 A | | 4/1998 | Murtagh, Jr. et al. |
| 5,856,144 A | | 1/1999 | Mierendorf et al. |
| 5,859,231 A | | 1/1999 | Shaw et al. |
| 6,087,103 A | | 7/2000 | Burmer |
| 6,087,112 A | | 7/2000 | Dale |
| 6,140,086 A | | 10/2000 | Fox et al. |
| 6,258,533 B1 | | 7/2001 | Jones |
| 6,270,976 B1 | * | 8/2001 | Schmidt et al. ................ 435/6 |
| 6,495,318 B2 | | 12/2002 | Harney |

OTHER PUBLICATIONS

International Preliminary Examination Report dated Mar. 15, 2004, International Application Serial No. PCT/US02/30943.

Okada, et al., Efficient directional cloning of recombinant adenovirus vectors using DNA–protein complex, Nucleic Acids Research, 1998, 26(8):1947–1950.

Wong, et al., A novel method for producing partial restriction digestion of DNA fragments by PCR with 5–methyl–CTP, Nucleic Acids Research, 1997, 25(20):4169–4171.

Hsiao, Exonuclease III induced ligase–free directional subcloning of PCR products, Nucleic Acids Research, 1993, 21(23):5528–5529.

Mead, et al., A universal method for the direct cloning of PCR amplified nucleic acid, Bio/Technology, 1991, 9:657–663.

Marchuk, et al., Construction of T–vectors, a rapid and general system for direct cloning of unmodified PCR products, Nucleic Acids Research, 19(5):1154.

Holton, et al., A simple and efficient method for direct cloning of PCR products using ddT–tailed vectors, Nucleic Acids Research, 1990, 19(5):1156.

Putney, et al., A DNA fragment with an α–phosphorothioate nucleotide at one end is asymmetrically blocked from digestion by exonuclease III and can be replicated in vivo, 1981, 75(12):7350–7354.

Pelham, et al., Eur. J. Biochem., 1976, 67:247.

Uhlen, et al., Gene, 1983, 23:369.

Sassenfeld, et al., Bio Technology, 1984, 2:76.

Melton, et al., Nucleic Acid Res., 1984, 12:7035.

Evan, et al., Mol. Cell. Biol., 1985, 5:3610–3616.

Labeit, et al., A new method of DNA sequencing using deoxynucleoside alpha–thiotriphosphates, DNA, 1986, 5(2):173–177.

(Continued)

Primary Examiner—Kenneth R. Horlick
(74) Attorney, Agent, or Firm—Senniger Powers

(57) ABSTRACT

Amplification mixtures, kits, amplicons, kits and processes are provided for amplifying a nucleic acid. In particular, provided are processes which utilize an amplification mixture comprising a polymerase, a deoxynucleotidetriphosphate (dNTP) mixture which contains modified dNTPs, a first primer and a second primer. Further provided are dNTP mixtures which contain modified dNTPs for at least two of the four nucleotide triphosphates, which when incorporated into a polynucelotide, impart resistance to enzymatic degradation by an exonuclease at the sites of incorporation of the modified dNTPs. Also provided are the amplicons and vectors which incorporate the modified nucleotides.

66 Claims, 20 Drawing Sheets

OTHER PUBLICATIONS

Dyatkina, et al., Terminating substrates of DNA polymerases: synthesis and functional study, Nucleic Acids Symp. Ser., 1987, 18:117–120.

Labeit, et al., Meth. Enzymol., 1987, 155:166.

Nakamaye, et al., Direct sequencing of polymerase chain reaction amplified DNA fragments through the incorporation of deoxynucleoside alpha–thiotriphosphates, Nucl. Acids Res., 1988, 16(21):9947–9959.

Hopp, et al., Biotechnology, 1988, 6:1204.

Smith, et al., Gene, 1988, 67:31.

Saiki, et al., Science, 1988, 239:487–491.

Prickett, et al., Bio Techniques, 1989, 7:580.

Kolodziej, et al., Methods Enzymol., 1991, 194:508–519.

Kaluz, et al., Nucleic Acids Research, 1992, 20:4369–4370.

* cited by examiner

Lanes:
a) 100 bp ladder
b) Taq
c) REDTaq
d) AccuTaq LA
e) KlenTaq LA
f) Pfu Turbo
g) Vent
h) Deep Vent
i) Pwo
j) UlTma o dA, dG occupation of PCR product
as a function of [b dA/GTP]
[dC/TTP]= 0.1 mM, [o dA/GTP]=0.05 mM
[b dATP]+[b dGTP]=0.5 mM o-dA occupation= -70[b-dATP]+99.9
o-dG occupation= -170[b-dGTP]+100
o-dA=o-dG at [b-dATP]/[b-dGTP]=2.5

L-R insertant

R-L insertant

1. Uncut pBX
2. BamHI pBX
3. XbaI pBX
4. BamHI/XbaI pBX
5. BamHI pUC19
6. XbaI pUC19
7. BamHI/XbaI pUC19
8. Uncut pUC19

RECOMBINANT DNA PROCESSES USING A DNTP MIXTURE CONTAINING MODIFIED NUCLEOTIDES

This application claims priority to U.S. provisional patent application Ser. No. 60/325,612 filed Sep. 28, 2001 now abandoned, incorporated herein by reference.

FIELD OF INVENTION

The present invention relates to recombinant DNA processes using a deoxynucleotide triphosphate (dNTP) mixture containing modified dNTPs, which when incorporated into a polynucleotide, impart resistance against enzymatic degradation by an exonuclease at the sites of incorporation of the modified dNTPs.

BACKGROUND OF THE INVENTION

Many widely known recombinant DNA techniques involve replicating or amplifying DNA. One such example is the cloning of an insert DNA into a target DNA fragment. During this procedure, the target fragment is typically digested with a restriction enzyme such as EcoRI. Similarly, the insert DNA, having the gene of interest, is digested with the same enzyme. In one type of restriction enzyme digestion, cleavage of both the target DNA and insert DNA leaves overlapping 3' or 5' nucleotide fragments on each end. These cohesive, overlapping fragments or "sticky ends" are well-known properties of some restriction enzymes. Incubation of the target and insert DNA together at an appropriate temperature allows the insert DNA to noncovalently bind to the target DNA. The target DNA and insert DNA are held together by hydrogen bonding of the cohesive ends. Further incubation with an enzyme, such as DNA ligase, results in ligation of the insert DNA to the target nucleotide strand.

Another method of adding an insert nucleotide fragment into a target DNA is known as blunt-end ligation. Digestion with some restriction enzymes, such as SrfI (GCCC/GGGC), SmaI (CCC/GGG), or Eco RV (GAT/ATC) do not leave any 3' or 5' overhanging nucleotides at the enzyme splice site. These enzymes are known as "blunt-end" enzymes due to this feature of their enzymatic activity. After digestion, blunt-end restriction enzymes maintain single 5' "terminal" phosphates on both sides of the restriction site. These terminal 5' phosphates are required by DNA ligase for any subsequent religation of the digested DNA sequence.

The ExoClone™-PCR Cloning Kit (Sigma, St. Louis, Mo.) utilizes a method by which multibase sticky end ligations between PCR products and suitably cleaved plasmid DNA is accomplished. Amplified DNA inserts are produced using specially designed primers whose 5' ends are cohesive with EcoRI cleaved vectors, i.e., 5' pAATTC. A modified mix containing thiodeoxyguanosine triphosphate (sdGTP) and deoxyguanosine triphosphate (dGTP) is used to amplify high GC and long (up to 4 kb) targets. Because exonuclease III cleaves phosphorothioates extremely slowly, if at all, digestion with exonuclease III exposes the bases of the 5' termini which are cohesive with the EcoRI digested vectors. This method is limited to cloning DNA into EcoRI cleaved vectors because the EcoRI recognition site is the only commonly used restriction site whose 5' four base overhang is punctuated by a base, i.e., guanine, not represented within the 5' pAATTC overhang.

Several methods have been devised for preferentially cloning insert DNA fragments into target sequences in one orientation. These methods are commonly known as directional cloning techniques and have been devised to position genes in the correct 5→3' orientation. Directional cloning is commonly performed by digesting the target nucleotide sequences with two different restriction enzymes. This method results in a molecule with dissimilar DNA ends at the target insertion site. The insert DNA is then digested with the same two restriction enzymes thereby having two dissimilar DNA ends that correspond to a specific orientation in the target insertion site. By following this procedure, the insert DNA only binds to the target sequence in one orientation.

Another method of directionally cloning an insert into a target sequence uses an exonuclease, such as Exonuclease III, to create the "sticky ends". See Kaluz, et al., *Nucleic Acids Research*, 1992, 20:4369–4370; U.S. Pat. Nos. 5,580,759, 5,518,901, 5,688,669 and 5,744,306. In this method, insert DNA fragments are digested with exonuclease III, a double strand specific exonuclease that catalyzes the stepwise release of nucleotides from the 3' hydroxyl termini of double stranded DNA, to produce cohesive ends. Digestion with exonuclease III is performed at low temperatures for very short times, usually 30–90 seconds, in order to prevent excessive degradation. After a timed digestion, the insert fragments have 5' overlapping nucleotide tails. These 5' nucleotide tails are engineered so that the 5' ends hybridize in one orientation upon base pairing to the target plasmid DNA molecule thereby resulting in a relatively simple method of directional cloning. While the use of exonuclease III provides a relatively simple method for directional cloning, it may be difficult to control the length of the generated cohesive ends which may be critical when cloning small size insert DNA.

There are several drawbacks, however, with single restriction enzyme digestion cloning methods and double restriction enzyme digestion directional cloning methods. For instance, digesting both the target DNA and insert DNA with restriction enzymes can be time consuming and multiple enzyme digestions increase the risk that either the target or insert DNA sequence will be cleaved at an internal restriction site. It is preferable that the sequence of the target DNA be known so that restriction enzymes are not selected which would cleave the sequence at an internal restriction site. Additionally, some restriction enzymes cleave very poorly, or not at all, when their recognition sequence is at or near the termini of a DNA strand.

Accordingly, it is desirable to formulate reagents and components for use in cloning and other recombinant DNA methodologies which could be utilized independent of the sequence being replicated or amplified. Such formulations would obviate the need for tedious control of restriction digestion and at the same time have minimal impact on PCR amplification performance. The provision of such process and reagent mixtures would avoid tedious or expensive aspects of current directional cloning such as multiple restriction enzyme digestion, addition of extra nucleotides to the insert and/or the use of multiple primers or linkers.

SUMMARY OF THE INVENTION

One aspect of the present invention, therefore, is the provision of materials, processes and kits for synthesizing DNA from a target nucleic acid. Generally, the present invention relates to processes which incorporate modified deoxynucleotide triphosphates (dNTPs) into a nucleic acid. The incorporation of these modified dNTPs impart resistance against enzymatic degradation by an exonuclease at the site of incorporation of the modified dNTPs thereby protecting the amplified product from complete degradation.

Briefly, the present invention is directed to a process for directionally ligating a nucleic acid to an adaptor sequence. In this process, an amplification mixture comprising a polymerase, a dNTP mixture which comprises modified dNTPs for at least one of the four dNTPs comprising dATP, dCTP, dGTP, dTTP and analogs thereof, a first primer and a second primer are used. The first primer is complimentary to a portion of the first strand of the target nucleic acid and has a first terminus which is complimentary to a first ligation site sequence of the adaptor sequence. The second primer is complimentary to a portion of the second strand of the target nucleic acid and has a second terminus which is complimentary to a second ligation site sequence of the adaptor sequence.

The amplification mixture is used to amplify a target nucleic acid thereby producing an amplified product, or an amplicon, from the target nucleic acid sequence. The primers anneal to each strand of the nucleic acid and each primer is extended using a polymerase and the dNTP mixture. During the extension step of the PCR, the modified dNTPs are incorporated into the amplicons in lieu of one of the non-modified dNTPs. The incorporation of the modified dNTPs into the amplicon impart resistance against enzymatic degradation by an exonuclease at the site of incorporation of the modified dNTPs.

Each terminus of the amplicons is then digested with an exonuclease. The amplicons are protected from enzymatic degradation by the exonuclease at the sites of incorporation of the modified dNTPs and preferably, the termini of the digested amplicons terminate at the sites of incorporation of the modified dNTPs. After digestion with the exonuclease, the digested amplicons contain a single stranded overhang sequence at each terminus. The first single stranded overhang sequence and the second single stranded overhang sequence are complimentary to a first ligation site sequence and a second ligation site sequence in the first and second adaptor sequence, respectively.

The first or second single stranded overhang sequence of the digested amplicons is directionally ligated to either the first or second ligation site sequence of the adaptor sequence. In a preferred embodiment, the first and second ligation site sequences are restriction enzyme recognition sequences. After digestion with the exonuclease, the digested amplicons have a single stranded overhang sequences which are complimentary to either a first or second ligation site sequence in the first or second adaptor sequence. In one aspect of the present invention, the adaptor sequence is a cloning vector and the digested amplicons are directionally inserted into a cloning vector having a ligation site which is flanked by the first and second ligation site sequences. Preferably, at least 80% of the digested amplicons are inserted in only one direction into the cloning vector.

Another aspect of the present invention is the provision of a process for producing amplicons using the an amplification mixture comprising a polymerase, a dNTP mixture containing modified dNTPs for at least two of the four nucleotide triphosphates, a first primer and a second primer. The amplicons produced using the amplification mixture have a first and second termini complimentary to either a first or second ligation site sequence, and are resistant to exonuclease degradation at the sites of incorporation of the modified dNTPs.

A further aspect of the present invention is the provision of amplicons which have at least two modified dNTPs incorporated therein. The incorporation of the modified dNTPs protects the polynucleotide sequence by imparting resistance to enzymatic degradation by an exonuclease at the sites of incorporation of the modified dNTPs in the amplicon. Such amplicons have a first and second termini complimentary to either a first or second ligation site sequence of an adaptor sequence. Such amplicons have various uses, such as for the synthesis of RNA molecules and in vitro synthesis of proteins. Also provided are vectors containing an amplicon resistant to enzymatic degradation by an exonuclease.

A further aspect of the present invention is the provision of a kit for directionally ligating a nucleic acid to an adaptor sequence. These kits contain a dNTP mixture containing modified dNTPs for at least two of the four nucleotide triphosphates which during the extension step of the PCR, are incorporated into the amplification product in lieu of one of the non-modified dNTPs, and a set of instructions for using the dNTP mixture to directionally ligate a target nucleic acid to an adaptor sequence.

This dNTP mixture protects nucleotides from enzymatic degradation by an exonuclease thus increasing the efficiency and the ease of the cloning process. A further aspect of the present invention is to provide the dNTP mixture containing modified dNTPs for at least two of the four nucleotide triphosphates, which during the extension step of the PCR, are incorporated into the amplification product in lieu of one of the non-modified dNTPs.

Other objects and features will be in part apparent and in part pointed out hereinafter.

DETAILED DESCRIPTION

Figure 1:
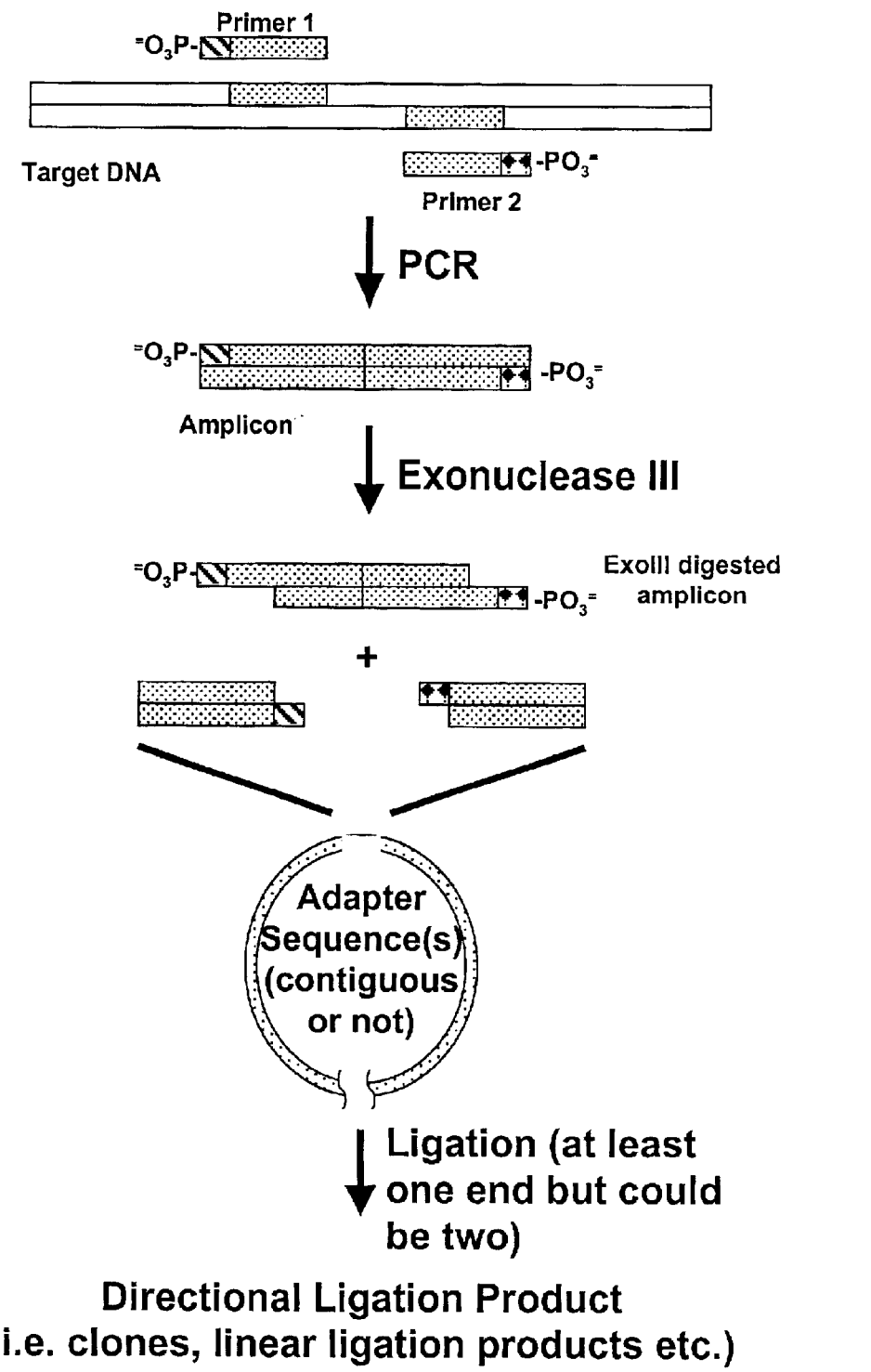
FIG. 1 is a flow chart schematically illustrating the directional cloning strategy in the present invention.

All publications, patents, patent applications or other references cited in this application are herein incorporated by reference in their entirety as if each individual publication, patent, patent application or reference are specifically and individually indicated to be incorporated by reference.

Definitions and Abbreviations

To facilitate understanding of the invention, a number of terms are defined below:

The "amplification" of nucleic acids refers to the replication of one to many additional copies of a nucleic acid sequence by a method catalyzed by an enzyme. Preferably, it is carried out using polymerase chain reaction (PCR) technologies. A variety of amplification methods are known in the art and are described, inter alia, in U.S. Pat. Nos. 4,683,195 and 4,683,202 and in *PCR Protocols: A Guide to Methods and Applications*, ed. Innis et al., Academic Press, San Diego, 1990. In PCR and other primer extension methodologies, a primer refers to a short oligonucleotide of defined sequence that is annealed to a DNA template to provide an initiation site for a polymerase as in the polymerase chain reaction.

A "polymerase" is a catalyst, usually a protein enzyme, for forming an extension of an oligonucleotide along a DNA template where the extension is complimentary to the template. A "polymerase" is an enzyme that is capable of incorporating nucleoside triphosphates to extend a 3' hydroxyl group of a nucleic acid molecule, if that molecule has hybridized to a suitable template nucleic acid molecule. Polymerase enzymes are discussed in Watson, J. D., In: Molecular Biology of the Gene, 3rd Ed., W. A. Benjamin, Inc., Menlo Park, Calif. (1977), which reference is incorporated herein by reference, and similar texts.

Exonuclease activity is, under the conditions of the reactions contemplated herein, the catalytic control or cleavage of nucleotides beginning at the end of a nucleic acid. A "3' to 5' exonuclease", or an enzyme having "3' to 5' exonuclease activity," begins the removal or cleavage of nucleotides at the 3' terminus of a nucleic acid and proceeds towards the 5' end. A "5' to 3' exonuclease", or an enzyme having "5 to 3' exonuclease activity", begins the removal or cleavage of nucleotides at a 5' terminus of a nucleic acid and proceeds toward the 3' end. There are enzymes that contain either 5' to 3' exonuclease activity or 3' to 5' exonuclease activity, or both activities in conjunction with polymerase activities that could be used in the processes disclosed herein.

"Complimentary" refers to the natural association of nucleic acid sequences by base-pairing (A-G-T pairs with the complimentary sequence T-C-A). Complementarity between two single-stranded molecules may be partial, if only some of the nucleic acids pair are complimentary, or complete, if all bases pair are complimentary.

The term "recognition sequence" refers to a particular sequence which a protein, chemical compound, DNA, or RNA molecule (e.g., restriction endonuclease, a modification methylase, or a recombinase) recognizes and binds. For example, a restriction enzyme recognition sequence is a nucleic acid sequence which a restriction enzyme will recognize, bind and cleave.

An "adapter sequence" is any duplex nucleotide sequence suitable for cohesive ligation to one of the ends of an exonuclease digested amplification product. Such adaptor sequences can result from enzymatic (in vivo or in vitro) or synthetic sources and can include but not be limited to cloning vehicles (plasmids, vectors, BACs etc.), amplification products and sequences prepared by non enzymatic means such as solid phase DNA synthesis.

The term "cloning vector" refers to a plasmid, virus, retrovirus, bacteriophage, cosmid, artificial chromosome (bacterial or yeast), or nucleic acid sequence which is able to replicate in a host cell which may contain an optional marker suitable for use in the identification of transformed cells, e.g., tetracycline resistance or ampicillin resistance. Optionally, a cloning vector may possess the features necessary for it to operate as an expression vector.

The term "dNTP" refers to deoxynucleoside triphosphates. The purine bases (Pu) include adenine (A), guanine (G) and derivatives and analogs thereof. The pyrimidine bases (Py) include cytosine (C), thymine (T), uracil (U) and derivatives and analogs thereof. Examples of such derivatives or analogs, by way of illustration and not limitation, are those which are modified with a reporter group, biotinylated, amine modified, radiolabeled, alkylated, and the like and also include phosphorothioate, phosphite, ring atom modified derivatives, and the like. The reporter group can be a fluorescent group such as fluorescein, a chemiluminescent group such as luminol, a terbium chelator such as N-(hydroxyethyl) ethylenediaminetriacetic acid that is capable of detection by delayed fluorescence, and the like.

The term sdNTP represents a thio deoxynucleotide wherein N=G, A, T or C.

The term bdNTP represents a borano deoxynucleotide wherein N=G, A, T, or C.

The term bdPuTP represents a borano-substituted purine.

The term bdPyTP represents a borano-substituted pyrimidine.

The term dPu represents a deoxypurine.

The term dPy represents a deoxypyrimidine.

The procedures disclosed herein which involve the molecular manipulation of nucleic acids are known to those skilled in the art. See generally Fredrick M. Ausubel et al. (1995), "Short Protocols in Molecular Biology," John Wiley and Sons, and Joseph Sambrook et al. (1989), "Molecular Cloning, A Laboratory Manual," second ed., Cold Spring Harbor Laboratory Press as incorporated herein by reference.

Accordingly, the present invention provides materials, processes and kits for directionally ligating a nucleic acid to an adaptor sequence. The processes and kits utilize an amplification mixture including a polymerase, a deoxynucleotide triphosphate (dNTP) mixture comprising modified dNTPs, a first primer and a second primer. A portion of the first and second primers are complimentary to the first and second strand of the double stranded target nucleic acid, respectively. The first primer has a first terminus which is complimentary to a first ligation site sequence of the first adaptor sequence and the second primer has a second terminus which is complimentary to a second ligation site sequence of a second adaptor sequence. The primers are extended using the dNTP mixture containing the modified dNTPs, which during the extension step of the PCR, are incorporated into the amplification product in lieu of one of the non-modified dNTPs. Amplicons are produced which contain the modified and non-modified dNTPs. The amplicons have a first and second terminus which are complimentary to the first ligation site sequence of a first adaptor sequence and the second ligation site sequence of a second adaptor sequence, respectively. The amplicons are contacted with an exonuclease which enzymatically degrades the amplicon by removing the non-modified nucleotides at the termini of the amplicons thereby exposing the sequences complimentary to either the first ligation site sequence of the first adaptor sequence and the second ligation site sequence of the second adaptor sequence. The first terminus of the digested amplicon is then ligated to the first ligation site sequence of the first adaptor sequence, and preferably, the second terminus of the digested amplicon is also ligated to the second ligation site sequence of the second adaptor sequence.

The present invention relates to processes for directionally ligating a nucleic acid to an adaptor sequence which utilize an amplification mixture to amplify a target nucleic acid thereby producing an amplified product, or an amplicon, from the target nucleic acid sequence. Preferably, the amplification mixture comprises a polymerase; a dNTP mixture comprising modified dNTPs for at least one of the four nucleotide triphosphates, i.e., dATP, dGTP, dCTP, dTTP and analogs thereof; a first primer; and a second primer. The amplicon is digested with an exonuclease and ligated to a first adaptor sequence. In one embodiment, the adaptor sequence is a cloning vector. Accordingly, one aspect of the present invention is directed to processes for cloning a nucleic acid into a cloning vector.

The target nucleic acid is amplified using methods of amplification known in the art. Any nucleic acid specimen can be utilized as the starting nucleic acid template. Thus, the amplification process may employ DNA or RNA, wherein DNA or RNA may be double or single stranded. In the event that RNA is to be used as a template, enzymes, and/or conditions optimal for reverse transcribing the template to DNA known to those in the art would be utilized. Preferably, the target nucleic acid is a double stranded DNA.

Several in vitro amplification techniques may be modified using methods known in the art, to use a DNA polymerase to enzymatically synthesize a DNA from the target nucleic acid, e.g., synthesis of RNA from DNA by transcription is followed by reverse transcription. Several suitable techniques include but are not limited to, the polymerase chain reaction (PCR) method, transcription-based amplification system (TAS), self-sustained sequence replication system (3SR), ligation amplication reaction (LAR), Qβ RNA replication system and run-off transcription. A preferred method of amplification is PCR amplification which involves an enzymatic chain reaction in which exponential quantities of the target nucleic acid are produced relative to the number of reaction steps performed. PCR amplification techniques and many variations of the PCR are known and well documented. See e.g., Saiki et al., *Science* 239: 487–491 (1988); U.S. Pat. Nos. 4,682,195, 4,683,202 and 4,800,159, which are incorporated herein by reference.

Typically, the selected nucleic acid, preferably, double stranded DNA, is denatured, thus forming single strands which are used as templates. One oligonucleotide primer is substantially complimentary to the negative (−) strand and another primer is substantially complimentary to the positive (+) strand. DNA primers are DNA sequences capable of initiating synthesis of a primer extension product. Primers "substantially complimentary" to each strand of the target nucleic acid sequence will hybridize to their respective nucleic acid strands under favorable conditions known to one skilled in the art, e.g., pH, salt concentration, cation concentration, temperature.

The primers used herein are complimentary to the first and second strand of the target nucleic acid to be amplified. The first primer contains a first terminus complimentary to a portion of the first strand of the target nucleic acid and complimentary to a first ligation site sequence of the first adaptor sequence. The second primer contains a second terminus complimentary to a portion of the second strand of the target nucleic acid and complimentary to a second ligation site sequence of the second adaptor sequence. The sequences of the first and second ligation site sequences of the first and second adaptor sequence are not identical and therefore, the sequences complimentary to the first and second ligation site sequences are not identical. It is not required that the sequence complimentary to a portion of the target nucleic acid and the sequence complimentary to the ligation site sequence of the adaptor sequence be exclusive of one another. Accordingly, two primers are utilized wherein the first terminus of the first primer is complimentary to a first ligation site sequence of the first adaptor sequence and the second terminus of the second primer is complimentary to a second ligation site sequence in the second adaptor sequence.

The first terminus of the first primer can be either a 3' terminus or a 5' terminus. Likewise, the second terminus of the second primer can be either a 3' terminus or a 5' terminus. In a preferred embodiment, the first terminus of the first primer is a 5' terminus which is complimentary to the first ligation site sequence in a first adaptor sequence and the second terminus of the second primer is a 5' terminus which is complimentary to the second ligation site sequence in the second adaptor sequence, wherein the 5' termini of the first and second primers are not identical.

It is preferred that the first primer's terminus which is complimentary to the first ligation site sequence of the first adaptor sequence be approximately between one and ten nucleotides in length, more preferably two to seven nucleotides in length, still more preferably two to five nucleotides in length, and most preferably four nucleotides in length. It is also preferred that the second primer's terminus which is complimentary to the second ligation site sequence of the second adaptor sequence be approximately between one to ten nucleotides in length, more preferably two to seven nucleotides in length, still more preferably two to five nucleotides in length, and most preferably four nucleotides in length. In a preferred embodiment, the 5' terminus of the first primer contains a four nucleotide sequence complimentary to a first ligation site sequence in the first adaptor sequence, and the 5' terminus of the second primer contains a four nucleotide sequence complimentary to a second ligation site sequence in the second adaptor sequence, wherein the 5' terminus of the first primer is not identical to the 5' terminus of the second primer.

Several methods are known in the art which are used to produce 5' overhang sequences. For example, 5' overhang sequences can be produced by a modification of the so called "exchange or replacement labeling" reaction. See Sambrook et al., "Molecular Cloning", Second Ed., page 5.39. This method utilizes a 3' to 5' exonuclease bearing DNA polymerase (typically T4 DNA polymerase) to burn back to the first occurrence of a single nucleotide included in the reaction mix.

In a preferred embodiment, the 3' or 5' termini of the first and second primers which are complimentary to the first and second ligation site sequences of the first and second adaptor sequence, respectively, are restriction enzyme recognition sequences. Many restriction enzymes are known in the art, such as those available from New England Biolabs, Beverly, Mass. Preferably, the 5' termini of the first and second primers contain restriction enzyme recognition sites corresponding to a restriction enzyme which leaves a 5' overhang restriction site. The 5' termini of the first and second primers contain restriction enzyme recognition sites which are not identical to each other. While 5' overhang restriction sites are preferred, the first and second primers termini containing restriction enzyme recognition sites corresponding to a restriction enzyme which leaves a 3' overhang restriction site may also be used.

In a preferred embodiment, the 5' terminus of the first primer sequence is an Acc65I, AflII, AgeI, AcaI, ApoI, AvrII, BamHI, BglII, BsiWI, EagI, EcoRI, HindIII, NcoI, NgoMIV, NheI, NotI, SalI, XbaI, XhoI or XmaI recognition sequence and the 3' terminus of the second primer sequence is an Acc65I, AflII, AgeI, AcaI, ApoI, AvrII, BamHI, BglII, BsiWI, EagI, EcoRI, HindIII, NcoI, NgoMIV, NheI, NotI, SalI, XbaI, XhoI or XmaI recognition sequence. Preferably, the sequences of the 5' termini of the first and second primer are not identical.

Annealing the primers to the denatured DNA templates is followed by extension with an enzyme to result in newly synthesized + and − strands containing the target DNA sequence. This annealing process consists of the hybridization of the primer to complimentary nucleotides of the DNA sequence template in a buffered aqueous solution. It is understood that the nucleotide sequence of the primer need not be completely complimentary to the portion of the DNA template in order to effectively anneal to the DNA template. The mixture containing the DNA templates is then heated to a temperature sufficient to separate the two complimentary strands of DNA. In a preferred embodiment, the mixture containing the DNA templates is heated to about 90 to 100° C. from about 0.5 to 10 minutes, even more preferably from 0.5 to 4 minutes to allow the DNA templates to denature and form single strands. The reaction mix is next cooled to a temperature sufficient to allow the primers to specifically anneal to sequences flanking the gene or sequence of interest. Preferably, the reaction mixture is cooled to 50 to 60° C., for approximately 0.5 to 5 minutes.

Preferably, the enzyme catalyzing the extension reaction is a polymerase, and more preferably, the polymerase used to amplify the target nucleic acid is a thermostable polymerase. Heat-stable (thermophilic) DNA polymerases are particularly preferred as they are stable when PCR is conducted in a single solution in which the temperature is cycled. Representative heat-stable polymerases are the DNA polymerases isolated from *Bacillus stearothermophilus* (Bio-Rad, Richmond, Calif.), *Thermus thermophilus* (FINZYME, ATCC #27634), *Thermus* species (ATCC #31674), *Thermus aquaticus* strain TV 1151B (ATCC #25105) and *Thermus filiformis* (ATCC #43280), the polymerase isolated from *Thermus flavus* (Molecular Biology Resources; Milwaukee, Wis.). Particularly preferred is Taq DNA polymerase available from a variety of sources including PerkinElmer, (Boston, Mass.), Promega (Madison, Wis.) and Stratagene (La Jolla, Calif.), and AmpliTaq™ DNA polymerase, a recombinant Taq DNA polymerase available from PerkinElmer.

The polymerase extends the primer by incorporating dNTPs from the dNTP mixture into the resulting polynucleotide, or amplicon. Preferred polymerases incorporate the modified dNTPs efficiently, base-specifically and independent of the surrounding sequence context. In a preferred embodiment, the polymerase used to amplify the target nucleic acid is Taq, REDTaq, AccuTaqLA, AmpliTaq™, KlenTaqLA, Ultma, Pwo, or Pfu and more preferably, Taq polymerase, REDTaq, AccuTaqLA and AmpliTaq™. A combination of two or more of the above polymerases such as, for example, a combination of Taq and Pfu, may also be used in the processes of the present invention. The temperature of the reaction mixture is then set to the optimum for the DNA polymerase to allow DNA extension to proceed.

The modified and unmodified dNTPs in the dNTP mixture are incorporated into the resulting polynucleotide, or amplicon. For use in a process of directionally ligating a nucleic acid to an adaptor sequence, the dNTP mixture comprises modified dNTPs for at least one of the four nucleotide triphosphates comprising dATP, dGTP, dCTP, dTTP and analogs thereof. In one preferred embodiment, the adaptor sequence is a cloning vector and the dNTP mixture for use in a process of cloning a nucleic acid into a cloning vector comprises modified dNTPs for at least two of the four nucleotide triphosphates comprising dATP, dGTP, dCTP, dTTP and analogs thereof. It will be appreciated that by virtue of the present invention that all modified dNTPs which serve as a substrate for a polymerase and protect nucleotides and/or the phosphodiester linkages between the nucleotides from enzymatic degradation by an exonuclease can be utilized in the dNTP mixture of the present invention. Preferably, any molecular manipulation, e.g., modifications to the base, sugar and/or phosphate, which produces a modified dNTP which serves as a substrate for a DNA polymerase and protects nucleotides and/or the phosphodiester linkages between the nucleotides from enzymatic degradation by an exonuclease can be utilized in the dNTP mixture of the present invention.

Preferably, the polymerase incorporates the modified dNTPs efficiently, base-specifically and independent of the surrounding sequence context. It is also preferred that the modified dNTPs in the dNTP mixture do not inhibit the enzyme catalyzed incorporation of the modified and unmodified dNTPs into the nucleotide sequence of the amplicon. Preferably, the modified dNTPs minimally affect the efficiency of the incorporation of the modified and unmodified dNTPs. In a preferred embodiment, the modified dNTPs reduce the efficiency of the polymerase incorporation of modified and unmodified dNTPs into the polynucleotide sequence of the amplicon by approximately 60%, more preferably, by approximately 70%, even more preferably by approximately 80%, and most preferably by approximately 90%. In a preferred embodiment, the modified dNTPs reduce the efficiency of the polymerase incorporation of modified and unmodified dNTPs into the polynucleotide sequence of the amplicon by less than 90%.

Preferably, the dNTP mixture comprises modified dNTPs wherein each modified dNTP is a fraction of the total amount of the particular deoxynucleotide triphosphate base in the dNTP mixture. In a process for directionally ligating a nucleic acid to a first adaptor sequence, the dNTP mixture contains modified dNTPs for at least one of the four dNTPs comprising dATP, dGTP, dCTP, dTTP and analogs thereof, preferably, the dNTP mixture contains modified dNTPs for at least two of th four dNTPs comprising dATP, dGTP, dCTP, dTTP and analogs thereof. $dNTP_1$ represents the at least one modified dNTP in the dNTP mixture, if two modified dNTPs are present in the dNTP mixture, $dNTP_2$ represents the second of the at least two modified dNTPs in the dNTP mixture, if three modified dNTPs are present in the dNTP mixture, $dNTP_3$ represents the third of the at least two modified dNTPs in the dNTP mixture, and if four modified dNTPs are present in the dNTP mixture, $dNTP_4$ represents the fourth of the at least two modified dNTPs in the dNTP mixture. Preferably, the dNTP mixture comprises modified dNTPs for at least two dNTPs, modified $dNTP_1$ and modified $dNTP_2$. Each modified $dNTP_1$ and modified $dNTP_2$ can be a modified dATP, modified dGTP, modified dCTP or modified dTTP, provided that $dNTP_1$ and $dNTP_2$ are not the same modified dNTP. The modified dNTPs are enzymatically incorporated into the amplicons in lieu of one of the non-modified dNTPs during primer extension. The modified dNTPs impart resistance by blocking the action of the exonuclease, for example, exonuclease III, or any other 3' to 5' exonuclease that cleaves normal phosphodiester linkages between the nucleotides but to which the modified dNTPs prove resistant.

In one embodiment, the dNTP mixture comprises three modified dNTPs, $dNTP_1$, $dNTP_2$ and $dNTP_3$, wherein each modified dNTP is a fraction of the total amount of the particular deoxynucleotide triphosphate base in the dNTP mixture. Each modified $dNTP_1$, $dNTP_2$ and $dNTP_3$ can be a modified dATP, modified dGTP, modified dCTP or modified dTTP, provided that $dNTP_1$, $dNTP_2$ and $dNTP_3$ are not the same modified dNTP. In another embodiment, the dNTP mixture comprises four modified dNTPs, $dNTP_1$, $dNTP_2$, $dNTP_3$ and $dNTP_4$, wherein each modified dNTP is a fraction of the total amount of the particular deoxynucleotide triphosphate base in the dNTP mixture. Each modified $dNTP_1$, $dNTP_2$, $dNTP_3$ and $dNTP_4$ can be a modified dATP, modified dGTP, modified dCTP or modified dTTP, provided that modified $dNTP_1$, $dNTP_2$, $dNTP_3$ and $dNTP_4$ are not the same modified dNTP. The modified dNTPs are enzymatically incorporated into the amplicons in lieu of one of the non-modified dNTPs during primer extension. The modified dNTPs impart resistance by blocking the action of the exonuclease, for example, exonuclease III, or any other 3' to 5' exonuclease that cleaves normal phosphodiester linkages between the nucleotides but to which the modified dNTP proves resistant.

In a process for directionally ligating a nucleic acid to a first adaptor sequence, the dNTP mixture contains modified dNTPs for at least one of the four dNTPs comprising dATP, dGTP, dCTP and dTTP. $dNTP_1$ represents the at least one modified dNTP in the dNTP mixture used specifically for directional ligation, and $dNTP_1$ can be a modified dATP, modified dGTP, modified dCTP or modified dTTP. In a preferred embodiment, the dNTP mixture utilized for directionally ligating a nucleic acid to an adaptor sequence comprises two modified dNTPs, modified $dNTP_1$ and $dNTP_2$. The modified dNTPs in the dNTP mixture are enzymatically incorporated into the amplicons in lieu of one of the non-modified dNTPs during primer extension. The modified dNTPs impart resistance by blocking the action of the exonuclease, for example, exonuclease III, or any other 3' to 5' exonuclease that cleaves normal phosphodiester linkages between the nucleotides but to which the modified dNTP proves resistant.

The dNTP mixture utilized in a process for directionally ligating a nucleic acid to an adaptor sequence comprises at least one modified dNTP comprising a modified dATP, modified dGTP, modified dCTP or a modified dTTP. Preferably, the at least one modified dNTP is a fraction of the total amount of the particular deoxynucleotide triphosphate base in the dNTP mixture. Preferably, the modified dNTPs are modified purines or pyrimidines, more preferably, the modified dNTPs are alpha phosphate modified purines or pyrimidines, even more preferably, alpha phosphate modified dATP or dGTP, and most preferably, alpha phosphate modified dGTP. In a preferred embodiment, the dNTP mixture utilized for directional ligation comprises at least one modified dNTP wherein the modified dNTPs are alpha boranophosphorano dNTPs or alpha thiophosphorano dNTPs, more preferably, the modified dNTPs are alpha boranophosphorano dNTPs. In another preferred embodiment, the modified dNTPs in the dNTP mixture utilized for directional ligation are alpha boranophosphorano dATPs, alpha boranophosphorano dGTPs, alpha thiophosphorano dATPs or alpha thiophosphorano dGTPs, more preferably, the modified dNTPs in the dNTP mixture are alpha boranophosphorano dATPs, alpha boranophosphorano dGTPs, and most preferably, the modified dNTPs are alpha boranophosphorano dGTPs.

Preferred nucleotide boranotriphosphates, e.g., 5'-alpha-boranotriphosphates and methods of synthesis are disclosed in U.S. Pat. Nos. 5,260,427, 5,659,027 and 5,683,869, and preferred nucleotide thiotriphosphates, e.g., 5'-alpha-thiotriphosphates and methods of synthesis are disclosed in Labeit et al., *Meth. Enzylmol.* 1987, 155: 166 and Nakamaye et al., *Nucl. Acids. Res.*, 1988, 16: 9947, the entirety of which are incorporated herein by reference. Once incorporated into the polynucleotide, thiophosphorodiester and boranophosphodiester bonds are resistant to exonuclease digestion.

Preferably, the dNTP mixture utilized to directionally ligate a nucleic acid to a first adaptor sequence comprises modified dNTPs for at least two of the four dNTPs comprising dATP, dGTP, dCTP and dTTP which are preferably modified purines, modified pyrimidines, or a combination of modified purines and pyrimidines. More preferably, the modified dNTPs in the dNTP mixture comprise alpha phosphate modified dNTPs, still more preferably, the modified dNTPs in the dNTP mixture comprise alpha phosphate modified purines, alpha phosphate modified pyrimidines or a combination of alpha phosphate modified purines and alpha phosphate modified pyrimidines, and most preferably, alpha phosphate modified dATP and dGTP. In a preferred embodiment, the modified dNTPs in the dNTP mixture comprise a combination of alpha boranophosphorano dNTPs and alpha thiophosphorano dNTPs, more preferably, the modified dNTPs in the dNTP mixture comprise alpha thiophosphorano dNTPs, and most preferably, the modified dNTPs in the dNTP mixture comprise alpha boranophosphorano dNTPs. In another preferred embodiment, the modified dNTPs in the dNTP mixture comprise a combination of alpha boranophosphorano dATP and dGTP and alpha thiophosphorano dATP and dGTP, more preferably, the modified dNTPs in the dNTP mixture comprise alpha thiophosphorano dATP and dGTP, and most preferably, the modified dNTPs in the dNTP mixture comprise alpha boranophosphorano dATP and dGTP.

The amount of the four nucleotide triphosphates in the dNTP mixture is determined by the concentration of modified dNTPs relative to the concentration of non-modified dNTPs. In a process for directionally ligating a nucleic acid to a first adaptor sequence, the dNTP mixture comprises modified dNTPs for at least one of four dNTPs comprising dATP, dCTP, dGTP and dTTP. Preferably, the amount of the four nucleotide triphosphates in the dNTP mixture utilized for directional cloning is determined by the ratio ($R_1$) of the concentration of modified $dNTP_1$ ([modified $dNTP_1$]) relative to the concentration of non-modified $dNTP_1$ ([$dNTP_1$]) which is shown as follows:

$$R_1=[\text{modified } dNTP_1]/[dNTP_1]$$

In a preferred embodiment, the ratio of the concentration of modified $dNTP_1$ relative to the concentration of non-modified $dNTP_1$ is less than 20, more preferably, the ratio is less than 9, and even more preferably, the ratio is less than 1.

Preferably, modified $dNTP_1$ in the dNTP mixture utilized in a process for directionally cloning a nucleic acid into a vector are modified purines, and more preferably, alpha phosphate substituted purines. In a preferred embodiment, the ratio of the concentration of alpha phosphate substituted $dNTP_1$ relative to the concentration of non-modified $dNTP_1$ is about 0.05 to 20, more preferably, the ratio is about 0.05 to 10, and most preferably, 0.05 to 4.

In a preferred embodiment, modified $dNTP_1$ is alpha thiophosphorano dATP, alpha thiophosphorano dGTP, alpha boranophosphorano dATP or alpha boranophosphorano dGTP, more preferably, $dNTP_1$ is alpha boranophosphorano dATP or alpha boranophosphorano dGTP, and most preferably, $dNTP_1$ is alpha boranophosphorano dGTP.

In a preferred embodiment, $dNTP_1$ in the dNTP mixture utilized to directionally ligate a nucleic acid to a first adaptor sequence are alpha thiophosphorano dNTPs, more preferably, alpha thiophosphorano dATP or dGTP and most preferably, alpha thiophosphorano dGTP. In one preferred embodiment, modified $dNTP_1$ is alpha thiophosphorano dATP and the ratio of the concentration of alpha thiophosphorano dATP relative to the concentration of non-modified dATP is 0.05 to 10, more preferably, 1.0 to 9, and most preferably, 1.5 to 5. More preferably, modified $dNTP_1$ is alpha thiophosphorano dGTP and the ratio of the concentration of alpha thiophosphorano dGTP relative to the concentration of non-modified dGTP is 0.05 to 10, more preferably, 0.05 to 7, and most preferably, 1.0 to 3.0.

In a more preferred embodiment, $dNTP_1$ in the dNTP mixture utilized to directionally ligate a nucleic acid to an adaptor sequence are alpha boranophosphorano dNTPs, more preferably, alpha boranophosphorano dATP or dGTP and most preferably, alpha boranophosphorano dGTP. Preferably, modified $dNTP_1$ is alpha boranophosphorano dATP and the ratio of the concentration of alpha boranophosphorano dATP relative to the concentration of non-modified dATP is 0.05 to 10, more preferably, 0.05 to 4, and most preferably, 0.01 to 2.0. In a more preferred embodiment, modified $dNTP_1$ is alpha boranophosphorano dGTP and the ratio of the concentration of alpha boranophosphorano dGTP relative to the concentration of non-modified dGTP is 0.05 to 20, more preferably, 0.1 to 10, and most preferably, 0.1 to 5.

In a preferred embodiment, the dNTP mixture comprises modified dNTPs for two of the four dNTPs, modified $dNTP_1$ and modified $dNTP_2$. Preferably, the amount of the four nucleotide triphosphates in the dNTP mixture is determined by the ratio ($R_2$) of the concentration of modified $dNTP_1$ ([modified $dNTP_1$]) to the concentration of modified $dNTP_2$ ([modified $dNTP_2$]) relative to the concentration of non-modified $dNTP_1$ ([$dNTP_1$]) to the concentration of non-modified $dNTP_2$ ([$dNTP_2$]) which is shown as follows:

$$R_2=([\text{modified } dNTP_1]/[\text{modified } dNTP_2])/([dNTP_1]/[dNTP_2])$$

In a preferred embodiment, the ratio of the concentration of modified $dNTP_1$ to the concentration of modified $dNTP_2$ relative to the concentration of non-modified $dNTP_1$ to the concentration of non-modified $dNTP_2$ is less than 51, more preferably, the ratio is less than 27, and even more preferably, the ratio is less than 13.

Preferably, the modified $dNTP_1$ and modified $dNTP_2$ in the dNTP mixture are modified purines and more preferably, alpha phosphate substituted dNTPs. In a preferred embodiment, the ratio of the concentration of alpha phosphate substituted $dNTP_1$ to the concentration of alpha phosphate substituted $dNTP_2$ relative to the concentration of non-modified $dNTP_1$ to the concentration of non-modified $dNTP_2$ is about 0.05 to 6.4, more preferably, the ratio is about 0.1 to 3.2, even more preferably, the ratio is about 0.2 to 1.6.

In a preferred embodiment, the two modified dNTPs in the dNTP mixture are alpha thiophosphorano dNTPs, and more preferably, alpha thiophosphorano dGTP and alpha thiophosphorano dATP. Preferably, the ratio of the concentration of alpha thiophosphorano dGTP to the concentration of alpha thiophosphorano dATP relative to the concentration of non-modified dGTP to the concentration of non-modified dATP is between 0.8 to 5.3, more preferably, the ratio is between 0.17 to 2.7, even more preferably, the ratio is between 0.33 to 1.33, and most preferably, the ratio is about 0.66.

In another preferred embodiment, the modified dNTPs in the dNTP mixture are alpha boranophosphorano dNTPs, and more preferably, alpha boranophosphorano dGTP and alpha boranophosphorano dATP. Preferably, the ratio of the concentration of alpha boranophosphorano dGTP to the concentration alpha boranophosphorano dATP relative to the concentration of non-modified dGTP to the concentration of non-modified dATP is between 0.05 to 6.4, more preferably, the ratio is between 0.1 to 3.2, even more preferably, the ratio is between 0.2 to 1.6, and most preferably, the ratio is about 0.4.

In another embodiment, the dNTP mixture comprises three modified dNTPs, $dNTP_1$, $dNTP_2$ and $dNTP_3$ wherein each modified dNTP is a fraction of the total amount of the particular deoxynucleotide triphosphate base in the dNTP mixture. Each $dNTP_1$, $dNTP_2$ and $dNTP_3$ is a modified dATP, dCTP, dGTP or dTTP, provided that $dNTP_1$, $dNTP_2$ and $dNTP_3$ are not the same modified dNTP. The amount of the four nucleotide triphosphates in the dNTP mixture comprising three modified dNTPs is determined by the ratio ($R_3$) of the product of the concentration of modified $dNTP_1$ ([modified $dNTP_1$]), the concentration of modified $dNTP_2$ ([modified $dNTP_2$]) and the concentration of modified $dNTP_3$ ([modified $dNTP_3$]) relative to the product of the concentration of non-modified $dNTP_1$ ([$dNTP_1$]), the concentration of non-modified $dNTP_2$ ([$dNTP_2$]) and the concentration of non-modified $dNTP_3$ ([$dNTP_3$]), which is shown as follows:

$$R_3=([\text{modified } dNTP_1]\times[\text{modified } dNTP_2]\times[\text{modified } dNTP_3])/([dNTP_1]\times[dNTP_2]\times[dNTP_3])$$

In order to determine the concentration of each modified $dNTP_1$, $dNTP_2$, and $dNTP_3$ in the dNTP mixture, an acceptable ratio of each modified and non-modified $dNTP_1$, $dNTP_2$, and $dNTP_3$ is individually determined by titration. An acceptable ratio is obtained when a compromise between amplification toxicity is minimized and protection against exonuclease digestion is maximized. In a preferred embodiment, this is when PCR amplification yield and quality is identical to reactions performed in the absence of any modified nucleotides while exonuclease protection is essentially quantitative, i.e., exonuclease digestion can result in a mean overhang length of less than 20 base pairs. It is possible however that a reduction in amplification yield may need to be tolerated so that adequate protection can be obtained. The type of experiment is exemplified in the s-dNTP and b-dNTP titrations shown in FIGS. 6 and 9. See "Quality Improvement through Planned Experimentation 2nd Edition", Ronald Moen, Thomas Nolan, Lloyd Provost, McGraw Hill, N.Y., 1998, incorporated herein by reference.

After the preferred concentration of each individual modified and non-modified $dNTP_1$, $dNTP_2$, and $dNTP_3$ is determined, the total mixture of modified and non-modified $dNTP_1$, $dNTP_2$, and $dNTP_3$ is determined by titration. The composition of the dNTP mixture containing modified dNTPs for three of the four dNTPs are obtained in a fashion analogous to that used for the determination of the relative ratios of solutions containing two modified dNTPs as described in Examples 3 and 4 and exemplified in FIG. 7. However, to determine the relative ratios of modified to non-modified dNTPs in a dNTP mixture comprising modified dNTPs for three of the four dNTPs, a three dimensional titration rather than two dimensional titration would be performed.

In another embodiment, the dNTP mixture comprises four modified dNTPs, $dNTP_1$, $dNTP_2$, $dNTP_3$ and $dNTP_4$ wherein each modified dNTP is a fraction of the total amount of the particular deoxynucleotide triphosphate base in the dNTP mixture. Each $dNTP_1$, $dNTP_2$, $dNTP_3$ and $dNTP_4$ is a modified dATP, dCTP, dGTP or dTTP, provided that $dNTP_1$, $dNTP_2$, $dNTP_3$ and $dNTP_4$ are not the same modified dNTP. The amount of the four nucleotide triphosphates in the dNTP mixture comprising four modified dNTPs is determined by the ratio ($R_4$) of the product of the concentration of modified $dNTP_1$ ([modified $dNTP_1$]), the concentration of modified $dNTP_2$ ([modified $dNTP_2$]), the concentration of modified $dNTP_3$ ([modified $dNTP_3$]) and the concentration of modified $dNTP_4$ ([modified $dNTP_4$]) relative to the product of the concentration of non-modified $dNTP_1$ ([$dNTP_1$]), the concentration of non-modified $dNTP_2$ ([$dNTP_2$]), the concentration of non-modified $dNTP_3$ ([$dNTP_3$]) and the concentration of non-modified $dNTP_4$ ([$dNTP_4$]), which is shown as follows:

$$R_4=([\text{modified } dNTP_1]\times[\text{modified } dNTP_2]\times[\text{modified } dNTP_3]\times[\text{modified } dNTP_4])/([dNTP_1]\times[dNTP_2]\times[dNTP_3]\times[dNTP_4])$$

In order to determine the concentration of each modified $dNTP_1$, $dNTP_2$, $dNTP_3$, and $dNTP_4$ in the dNTP mixture, an acceptable ratio of each modified and non-modified $dNTP_1$, $dNTP_2$, $dNTP_3$, and $dNTP_4$ is individually determined by titration. An acceptable ratio of each modified to non-modified dNTP is obtained when a compromise between PCR amplification toxicity is minimized and exonuclease protection is maximized. In a preferred embodiment, an acceptable ratio is obtained when PCR amplification yield and quality is identical to reactions performed in the absence of any modified dNTP in the dNTP mixture while exonuclease protection is essentially quantitative, i.e., exonuclease digestion results in a mean overhang length of less than 20 base pairs. However, sacrifices in amplification yield may need to be tolerated so that adequate exonuclease protection can be obtained. The type of experiment is exemplified in the s-dNTP and b-dNTP titrations shown in FIGS. 6 and 9. After the preferred ratio of each individual modified and non-modified $dNTP_1$, $dNTP_2$, $dNTP_3$, and $dNTP_4$ is determined, the total composition of modified and non-modified $dNTP_1$, $dNTP_2$, $dNTP_3$ and $dNTP_4$ in the dNTP mixture is determined by titration. The method for a dNTP mixture comprising four modified dNTPs are obtained using methods analogous to that utilized for the determination of the relative ratios of solutions containing two or three modified nucleotides as described in Examples 3 and 4 and exemplified in FIG. 7. A four dimensional titration rather than a two or three dimensional titration would be performed to determine the relative ratios of modified to non-modified dNTPs in a dNTP mixture comprising modified dNTPs for four dNTPs. See "Quality Improvement through Planned Experimentation 2nd Edition", Ronald Moen, Thomas Nolan, Lloyd Provost, McGraw Hill, N.Y., 1998, incorporated herein by reference.

An amplicon is produced from the extension of the primers when dNTPs, both modified and unmodified dNTPs, in the dNTP mixture are enzymatically incorporated into the nucleotide sequence of the amplicon. Thus, the newly synthesized amplicon contains both modified and unmodified dNTPs. The incorporation of the modified dNTPs impart resistance against enzymatic degradation by an exonuclease at the site of incorporation of the modified dNTPs thereby protecting the nucleotides of the amplicon from enzymatic degradation by an exonuclease.

The extension of the first and second primers using the dNTP mixture result in newly synthesized amplicons containing both modified and unmodified dNTPs which have a first terminus complimentary to a first ligation site sequence of the first adaptor sequence and a second terminus complimentary to a second ligation site sequence of a second adaptor sequence. Preferably, the amplicon's termini are amplified sequences which correspond to the 3' or 5' termini of the first and second primer sequences used in PCR. In a preferred embodiment, the first ligation site sequence of the first adaptor sequence and the second ligation site sequence of the second adaptor sequence are the ends of a cloning vector. Preferably, the termini of the amplicon are complimentary to the first and second ligation site sequences of the cloning vector, and more preferably, the 5' termini of the amplicons contain sequences complimentary to the first and second ligation site sequences of the cloning vector. In an even more preferred embodiment, the 5' termini of the amplicons contain restriction enzyme recognition sequences. Preferably, the termini of the amplicon contain restriction enzyme recognition sequences corresponding to restriction enzymes which leave a 5' overhang restriction site. In a preferred embodiment, the termini of the amplicon are not identical to each other to enable directional ligation into the cloning vector.

In order to prepare amplicons which can be inserted in one direction relative to the first adaptor sequence, the dNTP mixture comprising modified dNTPs for at least one, and preferably, two of the four dNTPs comprising dATP, dGTP, dCTP and dTTP is utilized to extend first and second primers which contain a first and second sequence, respectively, which is complimentary to a first and second ligation site sequence of the adaptor sequence, respectively. In a preferred embodiment, the first ligation site sequence of the first adaptor sequence and the second ligation site sequence of the second adaptor sequence are the ends of a cloning vector and the amplicons are prepared for directional cloning into the cloning vector.

The extension of the first and second primers using the dNTP mixture comprising modified dNTPs for at least one, and preferably, two of the four dNTPs result in newly synthesized amplicons containing both modified and unmodified dNTPs. The amplicons have a first terminus complimentary to a first ligation site sequence of the first adaptor sequence and a second terminus complimentary to a second ligation site sequence of the second adaptor sequence wherein the termini of the amplicon are not identical to each other. Preferably, the amplicon's termini are amplified sequences which correspond to the 3' or 5' termini of the first and second primer sequences used in PCR. In a preferred embodiment, the first and second ligation site sequences of the first and second adaptor sequences, respectively, are the ends of a cloning vector. Preferably, the termini of the amplicon are complimentary to the first and second ligation site sequences of the cloning vector, and more preferably, the 5' termini of the amplicons contain sequences complimentary to the first and second ligation site sequences of the cloning vector wherein the first and second ligation site sequences of the cloning vector are not identical. In an even more preferred embodiment, the 5' termini of the amplicons contain restriction enzyme recognition sequences. Preferably, the termini of the amplicon contain restriction enzyme recognition sequences corresponding to restriction enzymes which leave a 5' overhang restriction site.

The amplicons produced from this process have a variety of uses. For example, RNA transcripts are synthesized from the amplicons by in vitro DNA transcription. Transcription of RNA is performed with the appropriate RNA polymerase, preferably, T3, T7, or SP6, depending on the RNA polymerase promoter sites present upstream of the DNA to be transcribed. Because these polymerases are extremely promoter-specific, i.e., there is almost no transcriptional cross-talk, virtually homogenous RNA can be obtained using plasmid DNA (circular or linearized) or enzymatically synthesized DNA (linear) as the template in a transcription reaction. Melton et al. (Nucleic Acid Research (1984) v.12, p.7035) describes a general procedure for RNA synthesis in vitro. In short, DNA is mixed with an RNA polymerase plus the four ribonucleoside triphosphates used in RNA synthesis. During an incubation at 37° C., large amounts of the desired RNA are then generated by in vitro transcription. RNA transcripts may be radiolabeled with $^{32}$P-, $^{33}$P-, $^{35}$S- or $^{3}$H-labeled ribonucleotides, depending upon the specific application.

RNA transcripts may be used to generate probes for hybridization to Northern or Southern blots, plaque and colony lifts, tissue sections and chromosome spreads. RNA transcripts are also useful for S1 nuclease mapping, generation of antisense RNAs to block translation, and mRNA synthesis for translation in vitro.

Additionally, the amplicons may be used to synthesize protein expression in vitro. The in vitro synthesis of proteins in cell-free extracts is an important tool for molecular biologists and has a variety of applications, including the rapid identification of gene products, localization of mutations through synthesis of truncated gene products, protein folding studies, and incorporation of modified or unnatural amino acids for functional studies. The use of in vitro translation systems can have advantages over in vivo gene expression when the over-expressed product is toxic to the host cell, when the product is insoluble or forms inclusion bodies, or when the protein undergoes rapid proteolytic degradation by intracellular proteases.

The most frequently used cell-free translation systems consist of extracts from rabbit reticulocytes, wheat germ and *Escherichia coli*. All are prepared as crude extracts containing all the macromolecular components (70S or 80S ribosomes, tRNAs, aminoacyl-tRNA synthetases, initiation, elongation and termination factors, etc.) required for translation of exogenous RNA. Pelham et al. (Eur. J. Biochem. (1976) v.67, p.247) describe a general procedure for mRNA translation in vitro. In short, the lysates containing the cellular components necessary for protein synthesis are mixed with the subject mRNA and incubated at 30° C. for 90 minutes followed by an analysis of the translation reaction for expected products (i.e., SDS-PAGE analysis).

The amplicons containing modified dNTPs and unmodified dNTPs are preferably purified and treated with an exonuclease. Preferably, the amplicons were synthesized using a dNTP mixture comprising modified dNTPs for at least two of the four nucleotide triphosphates comprising dATP, dGTP, dCTP and dTTP and analogs thereof. Even more preferably, the amplicons were synthesized using a dNTP mixture comprising modified dATP and dGTP, and still more preferably, alpha thiophosphorano dATPs and dGTPs or alpha boranophosphorano dATPs and dGTPs, and most preferably, alpha boranophosphorano dATPs and dGTPs. Accordingly, in a preferred embodiment, the amplicons comprise alpha phosphate modified dATPs and dGTPs.

Because the modified dNTPs impart resistance to enzymatic degradation by blocking the action of an exonuclease that cleaves normal phosphodiester bonds, the exonuclease will only digest unmodified dNTPs which have been incorporated into the nucleotide sequence of the amplicon. Preferably, the enzymatic degradation by an exonuclease at the sites of incorporation of the modified dNTPs is approximately 1.1 to 10 times slower than exonuclease degradation of unmodified phosphodiester bond hydrolysis, more preferably, the enzymatic degradation by an exonuclease at the sites of incorporation of the modified dNTPs is approximately 10 to 1000 times slower than exonuclease degradation of unmodified phosphodiester bond hydrolysis, even more preferably the enzymatic degradation by an exonuclease at the sites of incorporation of the modified dNTPs is approximately 1000 to 10,000 times slower than exonuclease degradation of unmodified phosphodiester bond hydrolysis, and most preferably, the enzymatic degradation by an exonuclease at the sites of incorporation of the modified dNTPs is approximately 10,000 to 100,000 slower than exonuclease degradation of unmodified phosphodiester bond hydrolysis. In a preferred embodiment, the enzymatic degradation by an exonuclease at the sites of incorporation of the modified dNTPs is completely blocked at each modified phosphodiester bond of the amplicon. The amplicons are protected from enzymatic degradation by the exonuclease at the sites of incorporation of the modified dNTPs and preferably, the termini of the digested amplicons terminate at the sites of incorporation of the modified dNTPs. The exonuclease digests the termini of the amplicons thereby creating a single stranded overhang sequence at each terminus of the amplicon.

Preferably, the single stranded overhang sequence at the first terminus of the amplicon is complimentary to a first ligation site sequence of the first adaptor sequence, and the single stranded overhang sequence at the second terminus of the amplicon is complimentary to the second ligation site sequence of the second adaptor sequence. The sequences of the first and second ligation site sequences of the first adaptor sequence and the second adaptor sequence are not identical thereby enabling for the ligation of the digested amplicon in one direction relative to the first and second adaptor sequences. Preferably, the first and second ligation site sequences of the first and second adaptor sequences, respectively, are the ends of a doubly digested cloning vector and the digested amplicon is preferably inserted into the cloning vector in one direction relative to the vector, i.e., the digested amplicon is directionally cloned into the vector.

The amplicon is treated with an exonuclease, wherein the exonuclease can be a 5' to 3' exonuclease or a 3' to 5' exonuclease. In a preferred embodiment, the amplicons are treated with a 3' to 5' exonuclease, and more preferably, the amplicons are treated with exonuclease III. Treating the amplicons with exonuclease III digests the nucleotides of the 3' termini and exposes single stranded overhang sequences at each 5' terminus of the amplicons. Preferably, the single stranded overhang sequence at the first 5' terminus of the digested amplicon is similar, and preferably identical to the first primer's terminus which is complimentary to a first ligation site sequence of the first adaptor sequence; and the single stranded overhang sequence at the second 5' terminus of the digested amplicon is similar, and preferably identical to the second primer's terminus which is complimentary to a second ligation site sequence of the second adaptor sequence.

In a preferred embodiment, the single stranded overhang sequences at the first and second 5' termini of the digested amplicon are complimentary to the first and second ligation site sequences in the first and second adaptor sequence, respectively. Preferably, the single-stranded overhang sequence at the first and second 5' terminus is approximately between one and ten nucleotides in length, more preferably two to seven nucleotides in length, still more preferably two to five nucleotides in length, and most preferably four nucleotides in length. In a preferred embodiment, the single overhang sequence at the first and second 5' terminus of the digested amplicon has similar, and more preferably, the same number of nucleotides as the first and second ligation site sequence of the first and second adaptor sequences, respectively, and the single overhang sequence at the first and second 5' terminus of the digested amplicon is complimentary to the first and second ligation site sequence of the first and second adaptor sequences, respectively.

The single overhang sequence at the first 5' terminus of the digested amplicon is directionally ligated to the first adaptor sequence to form an amplicon-adaptor complex. Preferably, the adaptor sequence is a linear synthetic or enzymatically prepared linear nucleic acid. In a preferred embodiment, the single overhang sequence at the first and second 5' terminus of the digested amplicon is directionally ligated to the first and second ligation site sequence of the first and second adaptor sequences, respectively, thereby producing a digested amplicon flanked by a first and second adaptor sequence. In a preferred embodiment, the digested amplicon flanked by the first and second adaptor sequence is subjected to a second round of PCR amplification using primers which are specific for the first and second adaptors.

In a preferred embodiment, RNA is synthesized from the amplicon flanked by the first and second adaptor sequences by in vitro transcription. See Melton et al., *Nucleic Acid Res.*, 1984, 12: 7035. The synthesized RNA may be used to generate probes for hybridization to Northern or Southern blots, plaque and colony lifts, tissue sections and chromosome spreads. RNA transcripts are also useful for S1 nuclease mapping, generation of antisense RNAs to block translation, and mRNA synthesis for translation in vitro. In another preferred embodiment, the amplicon flanked by the first and second adaptor sequences is used to synthesize protein by in vitro translation. See Pelham et al., *Eur. J. Biochem.*, 1976, 67: 247.

In one preferred embodiment, the first and second ligation site sequences of the first and second adaptor sequences are the ends of a cloning vehicle such as a plasmid, vector, or bacterial artificial chromosome. These cloning vehicles may be used for subcloning and/or gene expression. Aside from being used to propagate the digested amplicon, the adaptor sequence may be designed to impart one or more desired properties that add functionality to the adaptor sequence.

Preferably, the adaptor sequence comprises a nucleotide sequence encoding for expression systems which will permit affinity purification. In a preferred embodiment, the adaptor sequence may comprise at least one epitope tag which may be c-myc, polyhistidine, polyarginine, glutathione-S-transferase (GST) tag, HA epitope, V5, Xpress™, and FLAG®. See Evan et al., *Mol Cell Biol.* 5:3610–3616 (1985). The use of a polyarginine tag allows for the polypeptide to be purified on a cation exchange resin. See Sassenfeld, H. M. and Brewer, S. J. *BioTechnology*, 2:76 (1984); U.S. Pat. No. 4,532,207. Preferably, the amplicon-adaptor complex includes a nucleotide sequence encoding for glutathione-S-transferase. The resulting polypeptide may be selectively recovered on glutathione-agarose. See Smith, D. B. and Johnson, K. S. *Gene* 67:31 (1988). In another preferred embodiment, the adaptor sequence comprises a nucleotide sequence encoding IgG-Sepharose can be used to affinity purify fusion proteins containing staphylococcal protein A. See Uhlen, M. et al. *Gene* 23:369 (1983). In yet another preferred embodiment, the adaptor sequence comprises a nucleotide sequence encoding the maltose-binding protein domain from the malE gene of *E. coli* which allows the affinity purification of the resulting polypeptide on amylose resins.

In a preferred embodiment, the adaptor sequence is designed to contain sequences encoding for a metal chelating sequence composed of multiple or alternating histidine residues which would allow the adaptor sequence to bind to a metal ion immobilized on a resin or other matrix. Preferably, a metal chelating sequence may comprise at least one histidine residue, at least one glycine residue or a combination of alternating or multiple histidine residues, which may be used in affinity purification techniques using a $Ni^{2+}$ binding metal resin. See e.g., U.S. Pat. Nos. 4,569,794, 5,310,663, 5,284,933 and 5,594,115 which are incorporated herein by reference. Once the polypeptide is bound to the metal resin, the adaptor sequence can be released by protonation of its associated metal ion-binding ligand. Dissociation is achieved by lowering the pH of the surrounding buffer medium, a common method known in the art for eluting bound proteins.

In another preferred embodiment, the adaptor sequence comprises nucleic acid sequences encoding for an epitope tag. Epitope tagging utilizes antibodies against guest peptides to study protein localization at the cellular level and subcellular levels. See Kolodziej, P. A. and Young, R. A., *Methods Enzymol.*, 194:508–519 (1991). Preferably, the digested amplicon is ligated to the first adaptor sequence comprising a nucleotide sequence encoding the epitope tag to form an amplicon-adaptor complex. The amplicon-adaptor complex is introduced into a cell by a method such as transformation. When the amplicon-adaptor complex is expressed the result is a chimeric protein containing the epitope as a guest peptide. If the epitope is exposed on the surface of the protein, it is available for recognition by the epitope-specific antibody, allowing the investigator to observe the protein within the cell using immunofluorescence or other immunolocalization techniques. Preferably, the amplicon-adaptor complex comprising such epitope tags are used for purifying proteins utilizing affinity purification techniques.

Preferably, the nucleotide sequence encoding the epitope tag is located at the terminus of the adaptor sequence. After the digested amplicon is directionally ligated to the adaptor sequence to form an amplicon-adaptor complex, the amplicon-adaptor complex is expressed. Preferably, the nucleotide sequence encoding the epitope tag is located at the terminus of the amplicon-adaptor complex, and more preferably, the nucleotide sequence encoding the epitope tag is located at the amino-terminus of the amplicon-adaptor complex. Generally, when the epitope is fused to the amino or carboxy-terminus of the expressed protein, the epitope is more accessible to the antibody for detection and less likely to cause severe structural or functional perturbations.

In a preferred embodiment, the adaptor sequence comprises a nucleotide sequence encoding for the FLAG® octapeptide Asp-Tyr-Lys-Asp-Asp-Asp-Asp-Lys (SEQ ID NO: 10). Preferably, the FLAG® epitope is fused to the amino or carboxy-terminus of the expressed amplicon-adaptor complex protein, and more preferably, the FLAG® epitope is fused to the amino terminus of the expressed amplicon-adaptor complex protein. The placement of FLAG® octapeptide at the amino-terminus allows for the amplicon-adaptor complex to be affinity purified on an immuno-affinity resin containing an antibody specific for the octapeptide. See Hopp, T. P., et al. *Biotechnology*, 6:1204 (1988); Prickett, K. S., et al., *BioTechniques*, 7:580 (1989); and U.S. Pat. No. 4,851,341. The original FLAG® sequence is recognized by two antibodies, M1, M2, and a FLAG® sequence with an initiator methionine attached is recognized by a third antibody, MS. The last five amino acids of the FLAG® sequence is a recognition site for the protease enterokinase, thus, allowing for removal of the FLAG® epitope. More preferably, the adaptor sequence comprises a nucleotide sequence encoding for multiple antigenic epitopes, and even more preferably, the adaptor sequence comprises a nucleotide sequence encoding for multiple FLAG® epitopes. See U.S. patent application Ser. No. 09/415,000, filed Oct. 8, 1999, incorporated herein.

The adaptor sequence may also comprise other elements such as promoters, repressors, or enhancers, e.g., BNL, CMV, T7, T3, SP6, Gal4, Tet On/Off. Preferably, the adaptor sequence comprises a reporting element, e.g., fluorescing proteins (e.g. GFP etc.), beta galactosidase (β-gal), luciferase, and/or an antibiotic resistant gene, (e.g. amp, neo, agr, kan, pur, hyg and etc.). The usage of a reporting gene allows for clone selection after the amplicon-adaptor complex is expressed. Other nucleotide sequences which may be included in the adapter nucleic acid are sequences that direct recombination or enable ligase independent cloning. The adaptor sequence may also be designed to include sequences critical to developing nucleic acid based diagnostics, increased specificity diagnostics, SNP analysis or gene expression analysis.

In one preferred embodiment, the digested amplicon is ligated to a cloning vehicle, and more preferably, a cloning vector. Preferably, the first and second ligation site sequences of the first and second adaptor sequences, respectively, are the ends of a cloning vector thereby resulting in a cloning vector comprising a ligation site flanked by a first and second ligation site sequence to which the digested amplicon may be ligated. The first and second ligation site sequences are complimentary to the single stranded overhang sequences at the first and second terminus of the digested amplicon, respectively, wherein the nucleotide sequences of the first and second ligation site sequences are not identical. The difference in the "sticky ends" or cohesive ends of each digested amplicon's termini and the complementarity between the first and second terminus of the digested amplicon and the first and second ligation site sequences, respectively, allow for the digested amplicons to be directionally inserted into the cloning vector.

Preferably, the synthesis of amplicons using a dNTP mixture comprising modified dNTPs followed by exonuclease digestion results in a higher preponderance of directional clones. In a preferred embodiment, a high percentage of the digested amplicons are inserted directionally into the cloning vector. Preferably, 80% of the digested amplicons are inserted directionally into the cloning vector, more preferably, 90% of the digested amplicons are inserted directionally into the cloning vector, and most preferably, 99% of the digested amplicons are inserted directionally into the cloning vector.

The resulting cloning vector is used to transform a host microorganism. The transformants are isolated and analyzed for the presence of the target nucleic acid. The transformants are then multiplied in culture to cause replication of the vector. Various procedures and materials for preparing recombinant vectors, transforming host cells with the vectors, replicating the vector and expressing polypeptide and proteins are discussed by Old and Primrose, Principles of Gene Manipulation, (2d Ed. 1981).

The digested amplicon may be inserted into any of a variety of conventional cloning vectors. Although plasmids are preferred, the vector may be alternatively a bacteriophage or cosmid. If cloning takes place in mammalian or plant cells, viruses can be used as vectors. If a plasmid is employed, it may be obtained from a natural source or artificially synthesized. The particular plasmid chosen should be compatible with the particular cells serving as the host, whether a bacteria such as Escherichia coli (E. coli), yeast, or other unicellular microorganism. The plasmid should have the proper origin of replication (replicon) for the particular host cell chosen. Any variety of cell that is transformable may serve as a host cell. Examples include but are not limited to, E. coli XL1-blue, DH5-α, HB101, JM101, JM103, JM109, etc. Other bacterial hosts may include Bacillus or Pseudomonas species and the like. By way of example, eukaryotic host cells may include Saccharomyces species.

This invention also contemplates kits for directional ligation of a nucleic acid to an adaptor sequence. This invention further contemplates kits for cloning of a nucleic acid to an adaptor sequence. Such kits may include, for example, the dNTP mixture, instructions for using the dNTP mixture and other components necessary for directional ligation or for cloning. The kit may be in the form of a test kit, that is, in a packaged collection or combination as appropriate for the needs of the user and any analytical instrumentation involved. Minimally, the kit will comprise the dNTP mixture comprising modified dNTPs which, when incorporated into a polynucleotide, impart resistance against enzymatic digestion by an exonuclease at the sites of incorporation of the modified dNTPs. Preferably, the kit furthers contain an exonuclease, preferably a 3' to 5' exonuclease, and more preferably, exonuclease III. The kit can, of course, also include appropriate packaging, containers, labeling, buffers, and controls for directional ligation of a nucleic acid to an adaptor sequence or for cloning a nucleic acid into a cloning vector.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

In vitro Incorporation of Thiodeoxypurines into DNA Using Polymerases

The universality with respect to thermostable polymerase was checked using a variety of commercially available polymerases. The experiment was performed with respect to product quality and quantity for a normal (0.8 mM dNTP) vs. thiodeoxypurine containing dNTP (sdNTP) mix. The experiment was carried out using buffers and reagents with the exception of the nucleotide mix as described or supplied by the enzyme supplier. Taq, REDTaq, AccuTaqLA, KlenTaqLA were obtained from Sigma-Aldrich, St. Louis, Mo. Pfu Turbo was obtained from Startagene. Vent and Deep Vent were obtained from New England Biolabs. Pwo was obtained from Roche. UlTma was obtained from Perkin Elmer. Amplification products were analyzed on a 0.2 agarose gel and visualized by ethidium bromide staining. No attempt was made to optimize cycling parameters for any particular enzyme.

Figure 2:
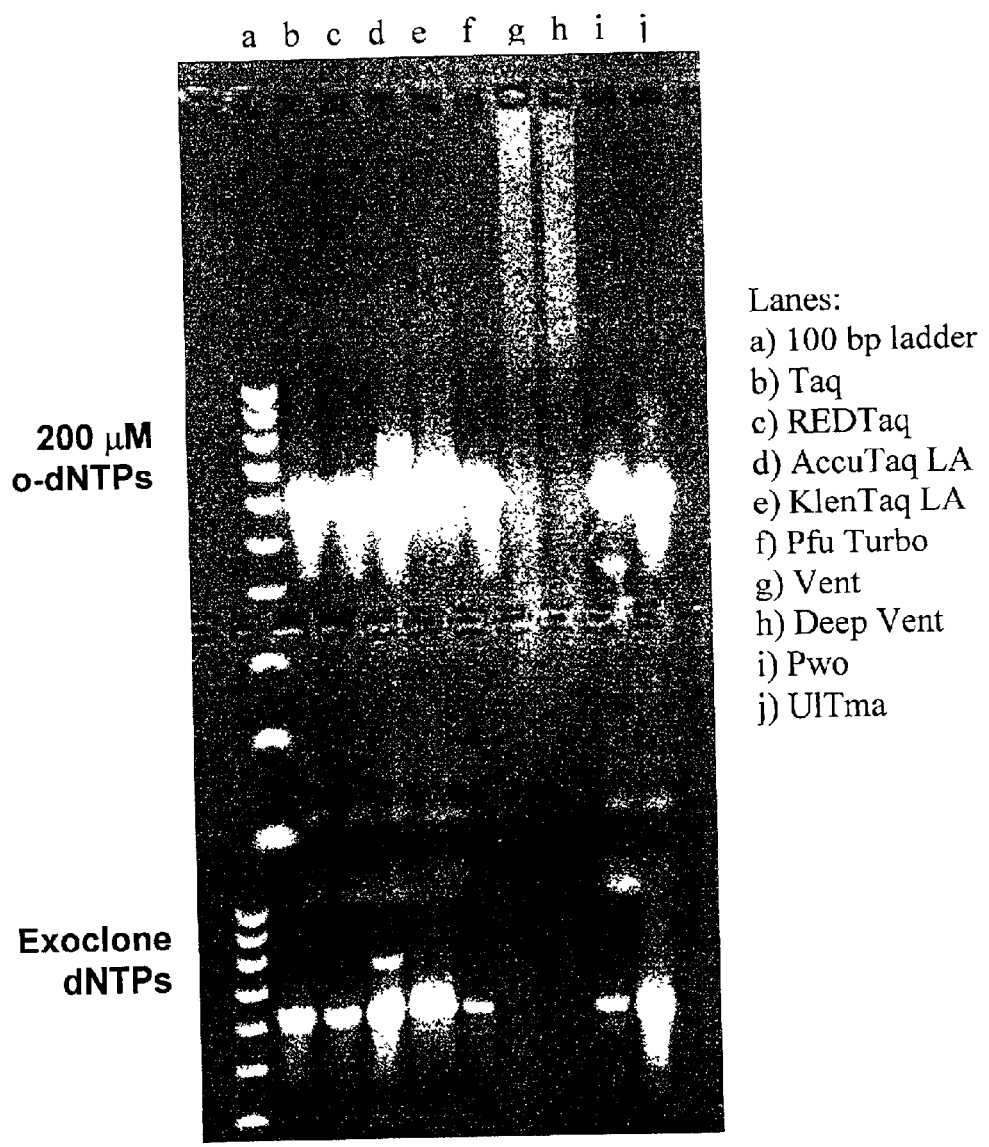
FIG. 2 is a photograph of a DNA agarose gel illustrating that product quality was independent of dNTP mixture, i.e., the product from a PCR reaction using unmodified dNTPs did not differ substantially from a reaction in which alpha thiophosphorano dATPs (sdATP) and dGTPs (sdGTP) were substituted for a fraction of unmodified dATP and dGTPs. The dNTP mixture was prepared as further described in Example 1.

FIG. 2 demonstrates that product quality was independent of nucleotide mix as the products from a normal vs. osdNTP were identically composed. Vent/Deep Vent lack of product was not followed up since neither enzyme is licensed for PCR and each have a reputation for being problematic. Notably from the gel, all enzymes seem to have somewhat of a reduced yield using the sdNTP mix formulation.

Figure 3:
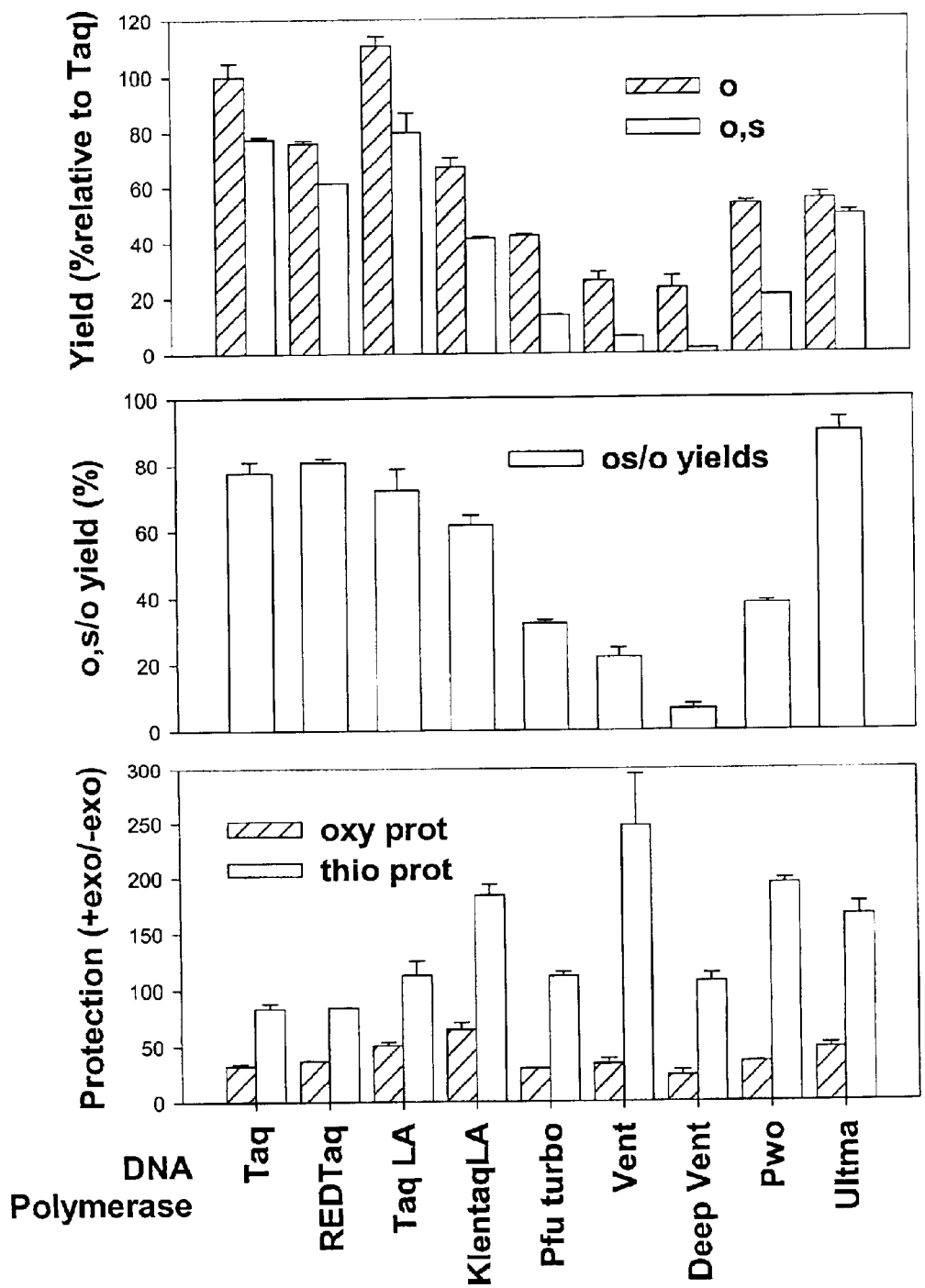
FIG. 3 contains graphs summarizing the amplification and protection yields from a $^{32}$PdNTP containing PCR. Yields were measured by TCA precipitation. The top panel shows overall yields of amplification (incorporation) products for all enzymes normalized to Taq/sdNTP. The middle panel shows yields of sdNTP products normalized to dNTP. Lower panel shows that while all products were degraded from approximately 50% or less (+Exo/−Exo) for all the deoxynucleotide amplifications, addition of ExoIII to the thiodeoxypurine (sdPuTP) containing reactions resulted in protections ranging from approximately 80 to 250%.

FIG. 3 summarizes the amplification and protection yields from a $^{32}$P dNTP containing PCR. Yields were measured by TCA precipitation. The top panel shows overall yields of amplification (incorporation) products for all enzymes normalized to Taq/dNTP. Yields were generally within 2× of Taq. The middle panel shows yields of sdNTP products normalized to dNTP. The inclusion of thiodeoxypurines resulted in a reduction of amplicon yield for all enzymes tested. The reduction is likely inconsequential for Taq, REDTaq, AmpliTaqLA, KlenTaq and Ultma.

Example 2

Stability of Phosphothioate Bonds to Hydrolysis by Exonuclease III

This experiment demonstrates that thiodeoxypurines incorporated into the amplicons demonstrated resistance to Exonuclease III hydrolysis. The lower panel of FIG. 3 demonstrates that while all products were degraded from approximately 50% or less (+exo/−exo) for the all deoxynucleotide amplifications, the addition of ExoIII to the thiodeoxypurine containing reactions resulted in protections ranging from approximately 80 to 250%.

Figure 4:
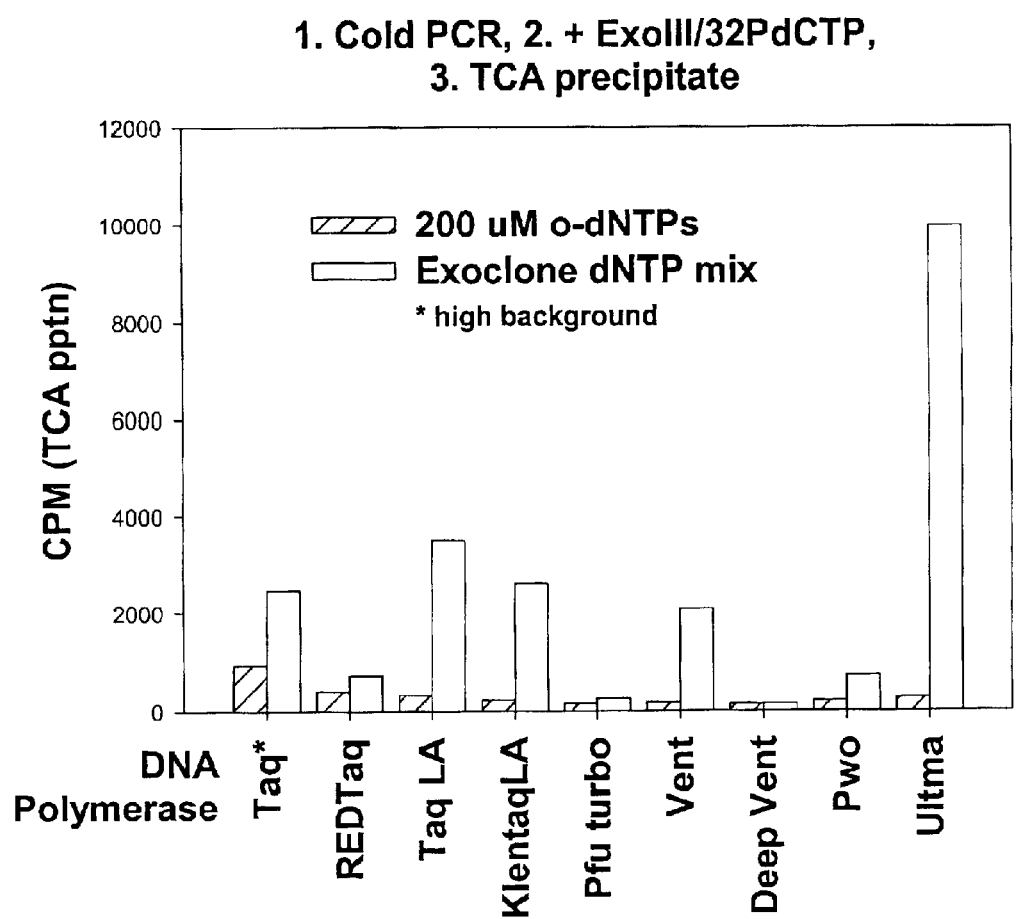
FIG. 4 is a graph illustrating that nucleotide protections that are greater than 100% could occur if the polymerase is active enough during ExoIII degradation to incorporate additional label potentially resulting in blunt-ended PCR products.

Protection of nucleotides greater than 100% may occur if the polymerase is active enough during ExoIII degradation to incorporate additional label. This was demonstrated by performing PCR in the absence of a labeled radionucleotide which was followed immediately by addition of the radionucleotide as part of the ExoIII addition (FIG. 4). Using the sdNTP mix, all enzymes incorporated nucleotides significantly above background.

Figure 5:
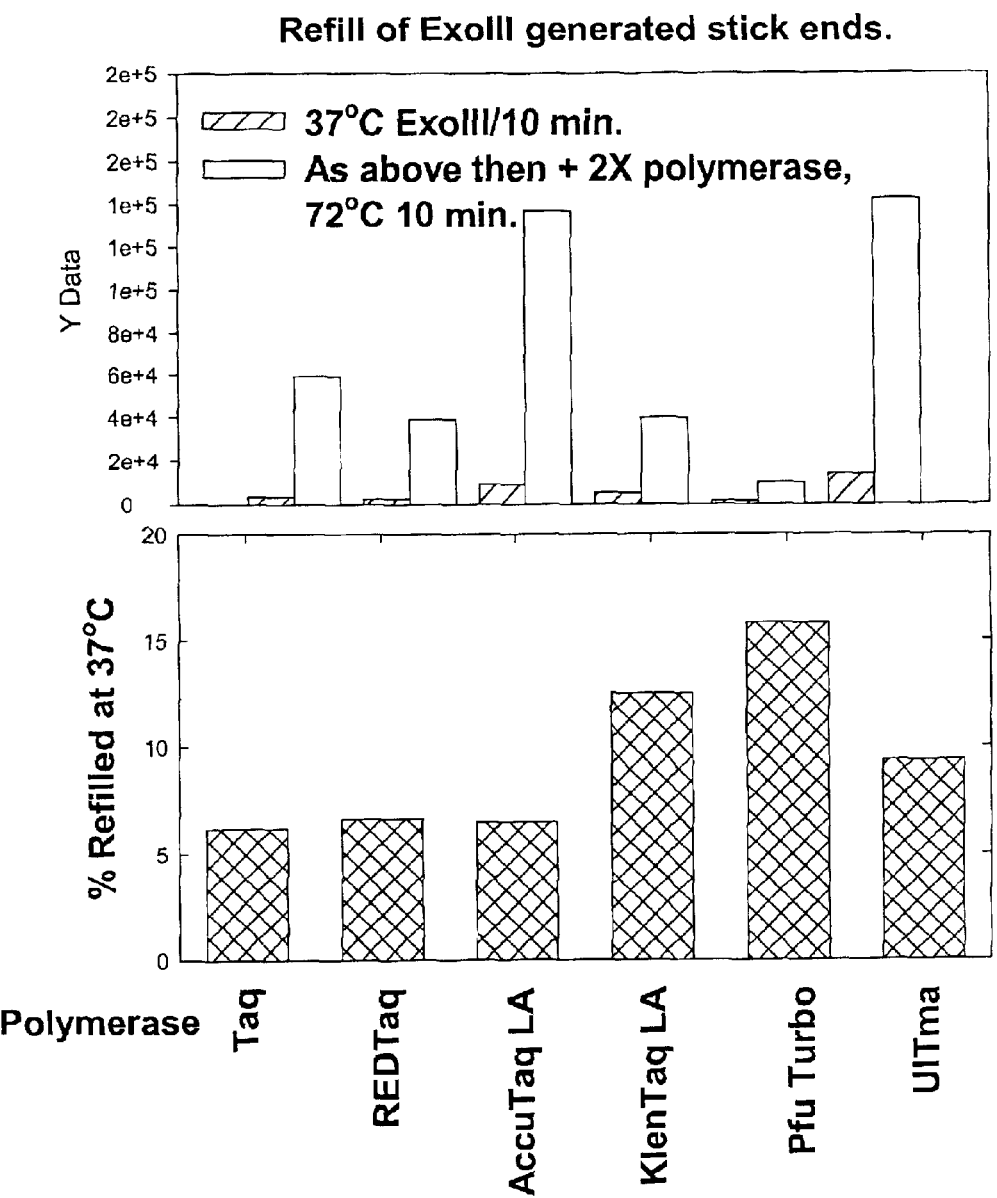
FIG. 5 contains graphs illustrating that re-incorporation during ExoIII digestion replaces an insignificant portion (approximately 5–15%) of the nucleotides removed by ExoIII. These data show it is safe to use the dNTP nucleotide mix with most thermostable DNA polymerases.

FIG. 5 demonstrates that ExoIII and polymerase were not competitively adding/removing nucleotides to produce an abundance of blunt ends. PCR was performed in the absence of labeled dNTP followed by addition of ExoIII/$^{32}$PdCTP. Taq DNA polymerase was added to half of the samples and followed by incubation at 72° C. to completely fill in the ExoIII generated 5' overhangs. As shown, re-incorporation during ExoIII digestion replaced an insignificant portion (approximately 5–15%) of the nucleotides removed by ExoIII. These data demonstrated that it is safe to use the sdNTP nucleotide mix with most thermostable DNA polymerases.

Example 3

Optimization of Incorporation of Thiodeoxynucleotides and Exonuclease Digestion

The shortcoming of using a single nucleotide for controlling exoIII digestion is sequence specific over and under-digestion. For over-digestion it is conceivable that target sequences could be amplified that are under-represented by the exonuclease controlling nucleotide (e.g. low abundance dG sequences have a low occurrence of sdG occupation). In this event, over-digestion of the amplicon would result in a population of clonable duplex DNAs and single stranded-ligation competing sequences. Such a situation would undoubtedly result in diminished cloning efficiencies relative to single strand deficient duplex amplicons. This is most likely going to be problematic for relatively short and/or high AT (low GC) amplicons. Under-digestion results from incomplete exposure of the cohesive 5' ends upon exoIII digestion leading to reduced cloning efficiency from suboptimal insert: plasmid stoichometry and from competitive inhibitory duplexes. Using one modified nucleotide (sdGTP) produced amplicons whose sdG content was 30%. There was a 30% chance that every G position would be occupied by a thioG. Exonuclease III then has a 30% chance of stopping at each G. Palindromic restriction sites can contain between one and two dGs opposite dC of a 5' overhang. Table 1 contains the expected proportions of A, B and C after exoIII digestion of amplicons designed to be cloned between dG containing and non-dG containing restriction sites (one end probabilities) and between two dG contining sites (both ends). The main lesson from this exercise is that the concentration of competitive ends (column C) approaches and exceeds the concentration of desired amplicon (column A). With the exception of the both end-two dG containing restriction examples (Table 1 column B bold), amplicons B are of little concern.

TABLE 1

Reduction of ligation efficiencies due to 30% dGTPaS occupation.

| Fraction of digested amplicon[a] | | | | | | Recog- | |
|---|---|---|---|---|---|---|---|
| One end[b] | | | Both ends[c] | | | nition | |
| A | B | C | A | B | C | sequence[d] | Affected enzymes[e] |
| 0.7 | 0 | 0.3 | 0.49 | 0.09 | 0.42 | ˆCDDD | Bsp11I, AflIII, NcoI, StyI, DsaI, BspHI, SpeI, AvrII, StyI, NheI, XbaI |
| | | | | | | ˆDCDD | XhoI, AvaI, BsoBI, SmlI |
| | | | | | | ˆDDCD | HindIII, SfcI, ApaLI |
| | | | | | | ˆDDDC | DpnII, MboI, Sau3AI, BglII, BstYI, BamHI, BclI, BsiWI, Acc65I, BanI, BsrGI |
| 0.49 | 0 | 0.51 | 0.24 | 0.26 | 0.50 | NˆCGN | MaeII, AclI, BsaHI, MspI, HpaII, HinP1I, NarI, TaqI, ClaI, BspDI, XhoI, AvaI, BsoBI, SmlI, AccI, BstBI |
| | | | | | | NˆGCN | None |
| | | | | | | ˆCCGG | AgeI, BsrFI, BsaWI, XmaI, AvaI, BsoBI, NgoMIV, BsrFI, BspEI, BsaWI |
| | | | | | | ˆCGCG | MluI, AflIII, DsaI, BssHII |
| | | | | | | ˆGCGC | KasI, BanI |
| | | | | | | ˆGGCC | EagI, EaeI, Bsp120I | based upon 30% dGTPaS occupation.
Amplicon to be cloned into plasmid digested with non-dG overhang (e.g. EcoRI) and dG containing overhang (e.g. affected enzyme column).
Amplicon to be cloned into plasmid digested with two dG containing overhang restrioction enzymes (e.g. one or two enzymes from affected enzyme column).
D = not C, ˆ = cut position
Palindromic Tetra- and hexa-nucleotide recognition sequences table (New England Biolabs)

Having established that phosphorothioate bonds can provide protection from the hydrolytic action of exonuclease III, this experiment was undertaken to understand the possibility of formulating a PCR invisible nucleotide mixture that would produce uniformly gapped ligation products independent of sequence would have nuclease resistant phosphodiesters statistically represented at all positions. With phosphorothioates, this could be accomplished by including all four sdNTPs. The final total nucleotide concentration used in this formulation was 0.8 mM, a concentration that is commonly recommended in many PCR protocols. At this concentration, the free $Mg^{++}$ concentration should not change relative to a "normal" or typical PCR. It should be noted that the 0.8 mM concentration is only required if, as here, it is desired that the reaction formulation of the reaction buffer is to be ignored. It is possible that other nucleotide formulations could be investigated, however, it would be prudent to ascertain their effect on free magnesium concentration and adjust accordingly as PCR performance is often dependent on magnesium concentration.

Sequence independent gap size or probability would occur when all nucleotides are replaced by odNTPS at identical frequency. Such formulation would meet the following criteria:

$$0.8 \text{ mM} = [dATP] + [dCTP] + [dGTP] + [dTTP] + [sdATP] + [sdCTP] + [sdGTP] + [sdTTP]$$

and $$k_{As}[sdATP] = k_{Cs}[sdCTP] = k_{Gs}[sdGTP] = k_{Ts}[sdTTP]$$

wherein $k_{Ns}$=incorporation rate constant.

The possibility of formulating the above solution was to titrate PCRs (lambda 500 mer) with each thionucleotide. PCR was performed using lambda control primers (Perkin Elmer) and lambda DNA (Sigma) as template. All reagents (1×PCR buffer, 0.05 u/μl Taq DNA polymerase) with the exception of the nucleotide composition were from Sigma and used without modification. Cycling conditions were 94° C./30 sec., 68° C./30 sec., 72° C./60 sec. for 30 cycles.

Figure 6:
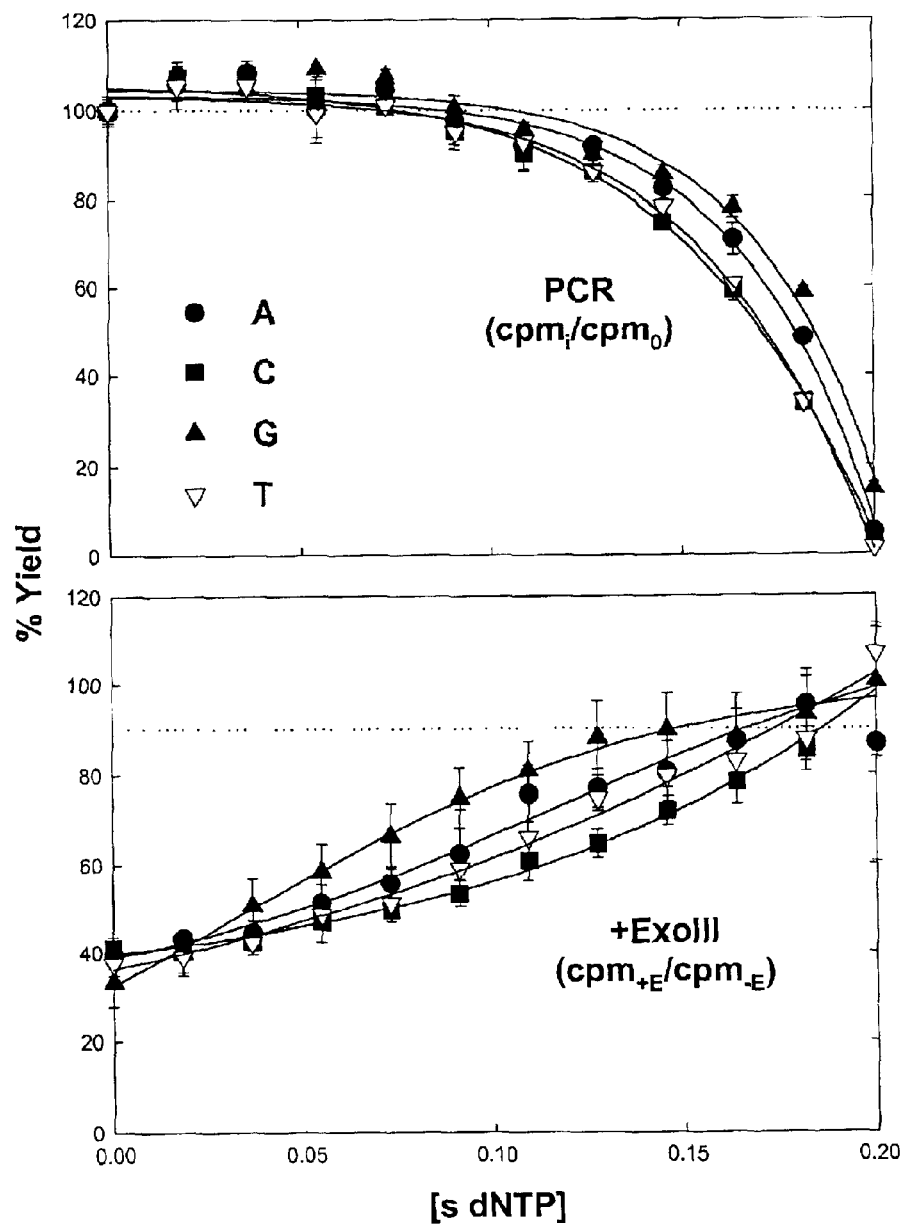
FIG. 6 contains graphs illustrating titration results for the four thionucleotides. The top panel illustrates that PCR is tolerant of thionucleotides in the order G>A>T=C. The lower panel (+ExoIII) reveals that the amplicons are preferentially protected from ExoIII digestion in the order G>A>T>C.

PCR was performed using an invariant $^{32}$PDN'TP tracer and 0.2 mM=[dNTP]+[sdNTP] (N and N' are not identical). Thionucleotide incorporation was ascertained by resistance to ExoIII digestion. As shown in the top panel of FIG. 6, PCR is tolerant of thionucleotides in the order G>A>T≈C. The lower panel of FIG. 6 shows that the amplicons were preferentially protected from exoIII digestion in the order G>A>T>C. PCR yield data indicated that the concentration of any of the dNTPs should remain above 0.1 mM in order to minimally impact PCR yield. This allowed for 0.4 mM to be available for sdNTP.

Supposing that each thionucleotide was equally distributed (i.e. [sdNTP]=0.1 mM each), then the concentrations of sdNTP would be sub-optimal for protection. Instead, thiopurines were chosen for optimization since they are best utilized by Taq during amplification. Although this relaxed the requirement for sequence independent ExoIII digestion termination, it still expanded the repertoire of sequences relative to the single thionucleotide example. The formulation criteria then became:

$$0.8 \text{ mM} = [dATP] + [dCTP] + [dGTP] + [dTTP] + [sdATP] + [sdGTP]$$

and $$k_{As}[sdATP] = k_{Gs}[sdGTP]$$

From the above thionucleotide titration yield data, the concentration of each dNTP was greater than or equal to 0.1 mM. PCR yields for a sdATP/sdGTP titration at [dNTP]= 0.125 mM each (N=A, C, G, T) were from ca. 85–92% (0.3 mM sdATP to 0.3 mM sdGTP) and PCR yields were 59–72% at [dNTP]=0.1 mM each. 100% was defined at [dNTP]=0.2 mM each for these experiments. From this data, an acceptable formulation would be:

$$[dNTP] = 0.125 \text{ mM each and } 0.3 \text{ mM} = [sdATP] + [sdGTP].$$

Figure 7:
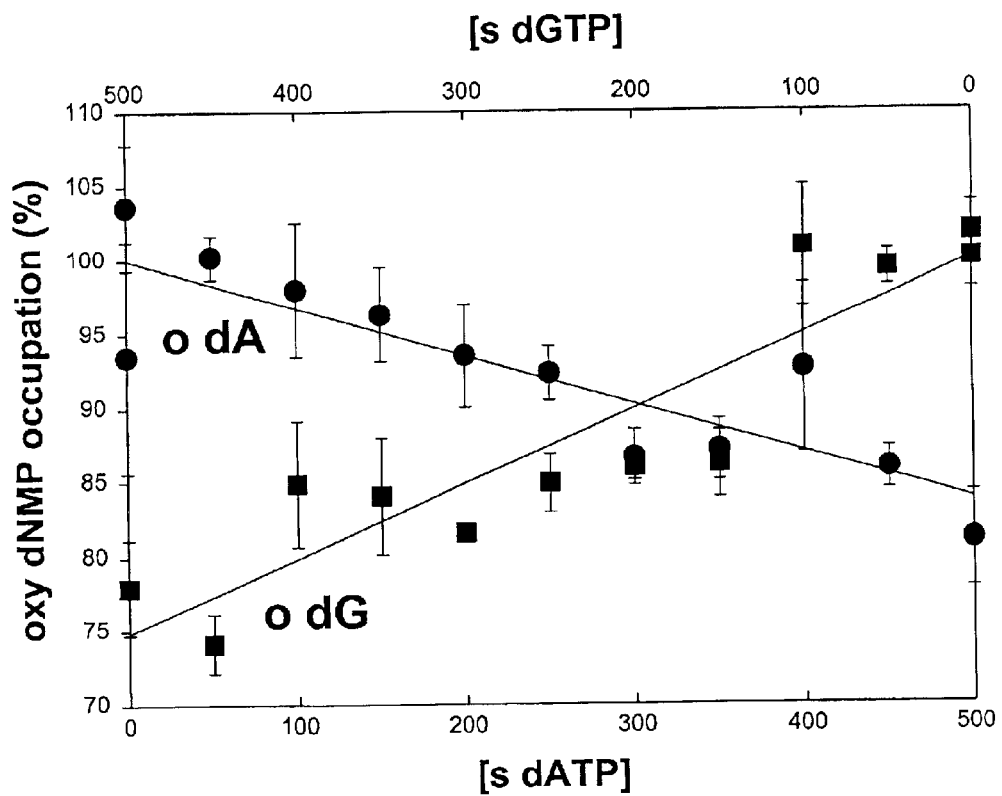
FIG. 7 is a graph illustrating the PCR reaction concentration ratios of alpha thiophosphano dATP (sdATP) to alpha thiophosphano dGTP (sdGTP) utilized to optimize modified dNTP incorporation.
Figure 8:
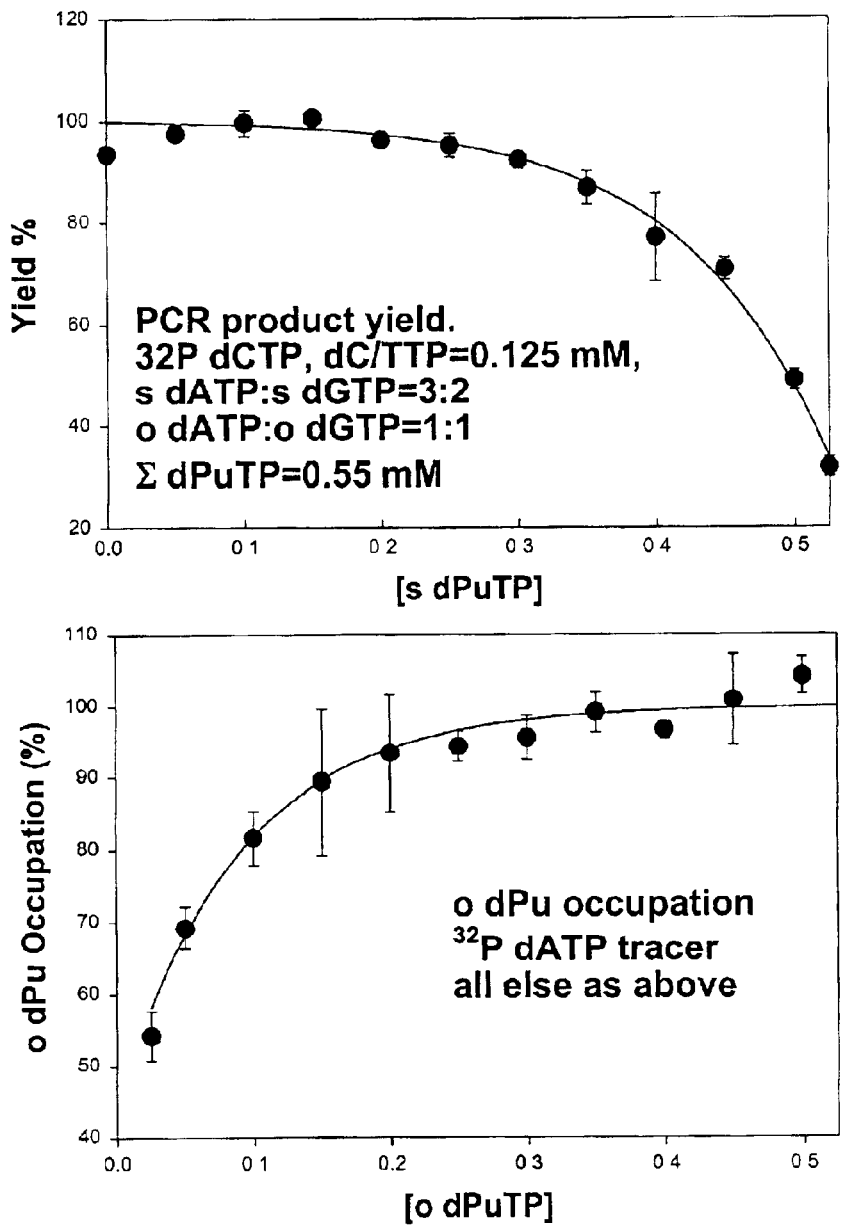
FIG. 8 contains graphs illustrating that PCR product yield begins to decrease at concentrations of thiodeoxypurine above 0.3 mM. The lower panel reports the occupation of purine sites by thiodeoxypurine monophosphate (sdPuMP) as a function of dPuTP concentration.

The optimal ratio of sdATP to sdGTP (i.e. such that $k_{As}[sdATP]=k_{Gs}[sdGTP]$) was measured as shown in FIG. 7. Although these conditions were not those used in the final formulation, the quantity measured is the ratio of thiodeoxypurines. Inspection of the figure revealed that $k_{As}$ [sdATP]=$k_{Gs}$[sdGTP] at 0.3 mM sdATP/0.2 mM sdGTP or [sdATP]/[sdGTP]=3/2. The formulation was finalized by titrating thiodeoxypurine (sdATP/sdGTP=3/2) vs. deoxypurine (dATP/dGTP=1). FIG. 8 (top panel) demonstrates that PCR product yield begins to suffer at concentrations of thiodeoxypurine above 0.3 mM. The final formulation was: [dNTP]=0.125 mM each, 0.18 mM [sdATP] and 0.12 mM [sdGTP]. The lower panel of FIG. 8 reports the occupation of purine sites by dPuMP as a function of dPuTP concentration. The above formulation produces amplicons that are 97% dPuMP/3% sdPuMP (i.e. DAMP occupation was 97% at [dPuTP]=0.25 mM). The expected 5' overhang length for a random sequence duplex is calculated as $(0.5+0.5*0.97)^n$ (i.e. 50% chance dPy plus 50% chance of 97% chance dPu at nucleotide position n). From this, it is apparent that all but very short amplicons should remain duplex after ExoIII digestion (data not shown).

In random sequence DNA, this nucleotide solution will produce amplicons that are 50% blocked to exoIII digestion by base 43. The probability of encountering a dG deficient sequence decrease as $0.75^n$ compared to a dPu deficient sequence at $0.5^n$ i.e., a dG deficient sequence is $1.5^n$ more likely than is a dPu deficient sequence. Table 2 demonstrates how quickly this difference manifests itself as a function of base position. The advantage of sdPu incorporation vs. sdG is given by:

$$(P_{notG}P_N)/(P_{notPu}P'_N)^n$$

where $P_{notG}$ is the probabilty of not G (i.e. is A, C or T), $P_N$ is probability of dNMP (A+C+G+T), $P_{notPu}$ is probability of not A or G (i.e. C+T), $P'_{oN}$ is probability of dNMP (A+C+G+T) or:

$$(0.75(0.75+0.25 P_{oG}))/(0.5(0.5+0.5 P_{oPu}))^n$$

where $P_{oG}$ and $P_{oPu}$ are the probabilities of an dGMP (70%) and dPuMP (97%) at base position n (column 3, Table 2). These data demonstrate that though specific base occupation has been reduced using sdPuTP, the effect is superior protection for a larger cross section of sequences.

TABLE 2

Relative probabilities of encountering dG vs dPu deficient sequences as a function base position

| Base Position | dG vs. dPu deficiency probabilities $(0.75/0.5)^n$ | sdPu vs. sdG advantage $(0.75(0.75 + 0.25 \times 0.7))/$ $(0.5(0.5 + 0.5 \times 0.97))^n$ |
|---|---|---|
| 1 | 1.5 | 1.4 |
| 5 | 7.59 | 5.6 |
| 10 | 57.7 | 31 |
| 15 | 438 | 170 |
| 20 | 3,325 | 960 |
| 25 | 25,251 | 5,400 |
| 30 | 191,751 | 30,000 |
| 35 | 1,456,109 | 160,000 |
| 40 | 11,057,332 | 930,000 |
| 45 | 83,966,617 | 5,200,000 |
| 50 | 637,621,500 | 29,000,000 |
| 55 | >human genome | $1.6 \times 10^8$ |

Table 3 contains expected proportions of "ligatable" ends from sdPuTP containing PCR products.

TABLE 3

Reduction of ligation efficiencies due to 6% sdPuTP occupation

| Fraction of digested amplicon[a] | | | | | | |
|---|---|---|---|---|---|---|
| One end[b] | | | Both ends[c] | | | |
| A | B | C | A | B | C | Recognition sequence[d] |
| N/A | N/A | N/A | 0.88 | 0.003 | 0.11 | ˆPuPuPyPy, ˆPuPyPuPy, ˆPyPuPyPu, ˆPyPyPuPu |
| N/A | N/A | N/A | 0.94 | 0.0009 | 0.058 | NˆPyPuN, NˆPuPyN |

[a] Calculated using 3% sdPuTP occupation.
All four base palindromes contain purines making it impossible to have an unaffected end.
Amplicon to be cloned into plasmid digested with one or two four base overhang producing restriction enzymes.
Pu = dA or dG, Py = dC or dT, ˆ = cut position A comparison of Tables 1 and 3 reveals that inclusion of an additional thionucleotide reduces the relative abundance of competitive ligation inhibitors to inconsequential levels. However, a nucleotide mixture containing a set of three or four modified nucleotides could be developed that would produce low enough occupancies at any position within the amplicon thereby retaining a minimization of competitive ligation inhibitors.

Although there was a loss in product yield using the osdNTP mix, the mix did not alter product quality relative to PCR using non-modified dNTP mixtures (data not shown).

Example 4

Optimization of Incorporation of bdNTPs and Exonuclease Digestion

The methods used to develop a phosphoroborano containing deoxynucleotide mix that rendered amplicons protected from exoIII overdigestion was analogous with the thiophosphate work described in Example 3. Specifically, 1) titration of all four phosphoroboranes in a quantitative PCR to establish nucleotide biases, 2) optimization of favored phosphoroborane ratios (i.e. bdATP, bdGTP), 3) titration of optimized phosphoroborane mixture with dNTPs. PCR was performed using lambda control primers (Perkin Elmer) and lambda DNA (Sigma) as template. All reagents (1×PCR buffer, 0.05 u/µl Taq DNA polymerase) with the exception of the nucleotide composition were from Sigma and used without modification. Cycling conditions were 94° C./30 sec., 68° C./30 sec., 72° C./60 sec for 30 cycles.

Figure 9:
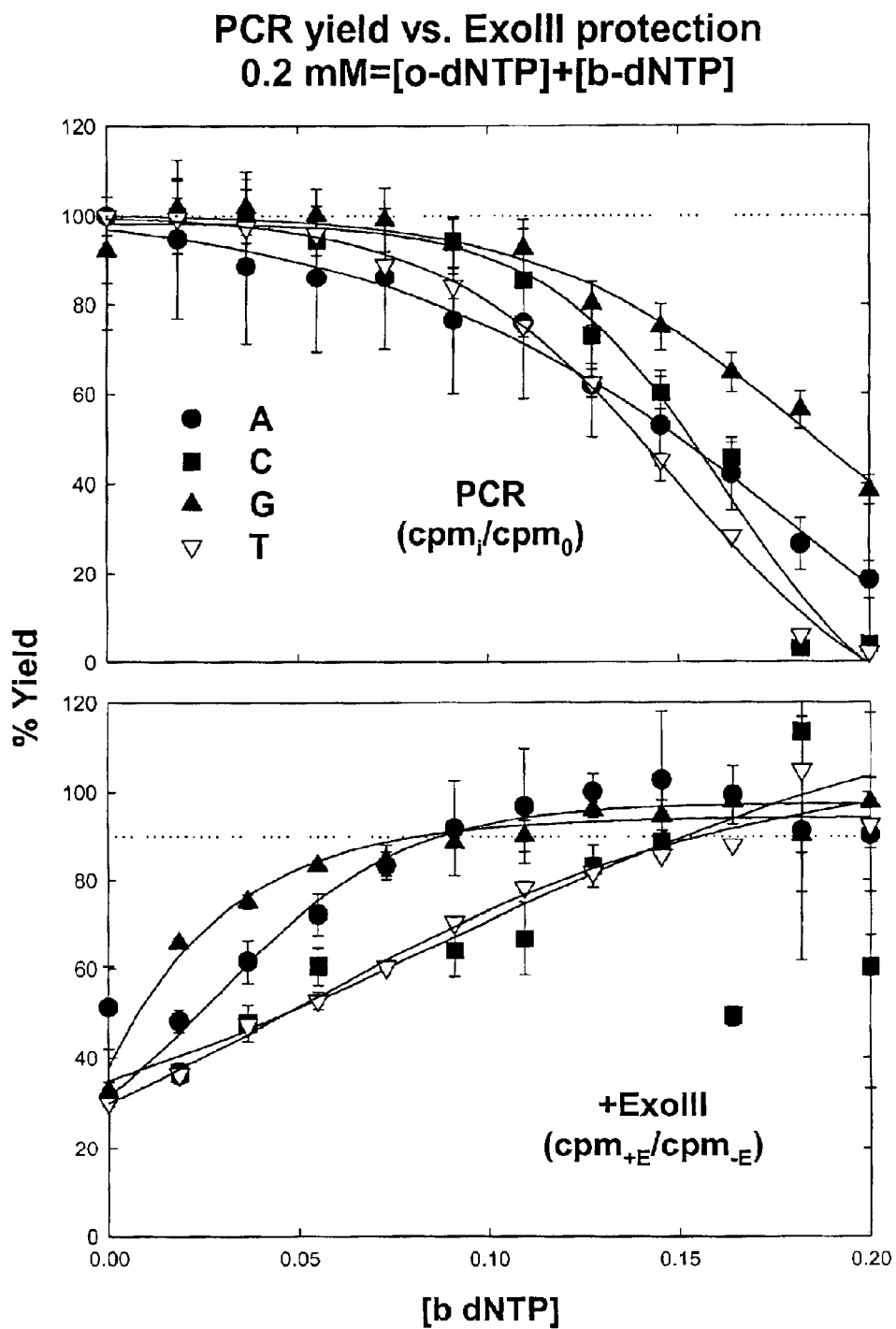
FIG. 9 contains graphs illustrating titration results for the four phosphoborane nucleotides (bdNTP, N=A, C, G, T). These data show that the PCR yields are negatively impacted by phosporoboranes in the order G<C<T<A and that ExoIII protection increases in the order G>A>C=T.
Figure 10:
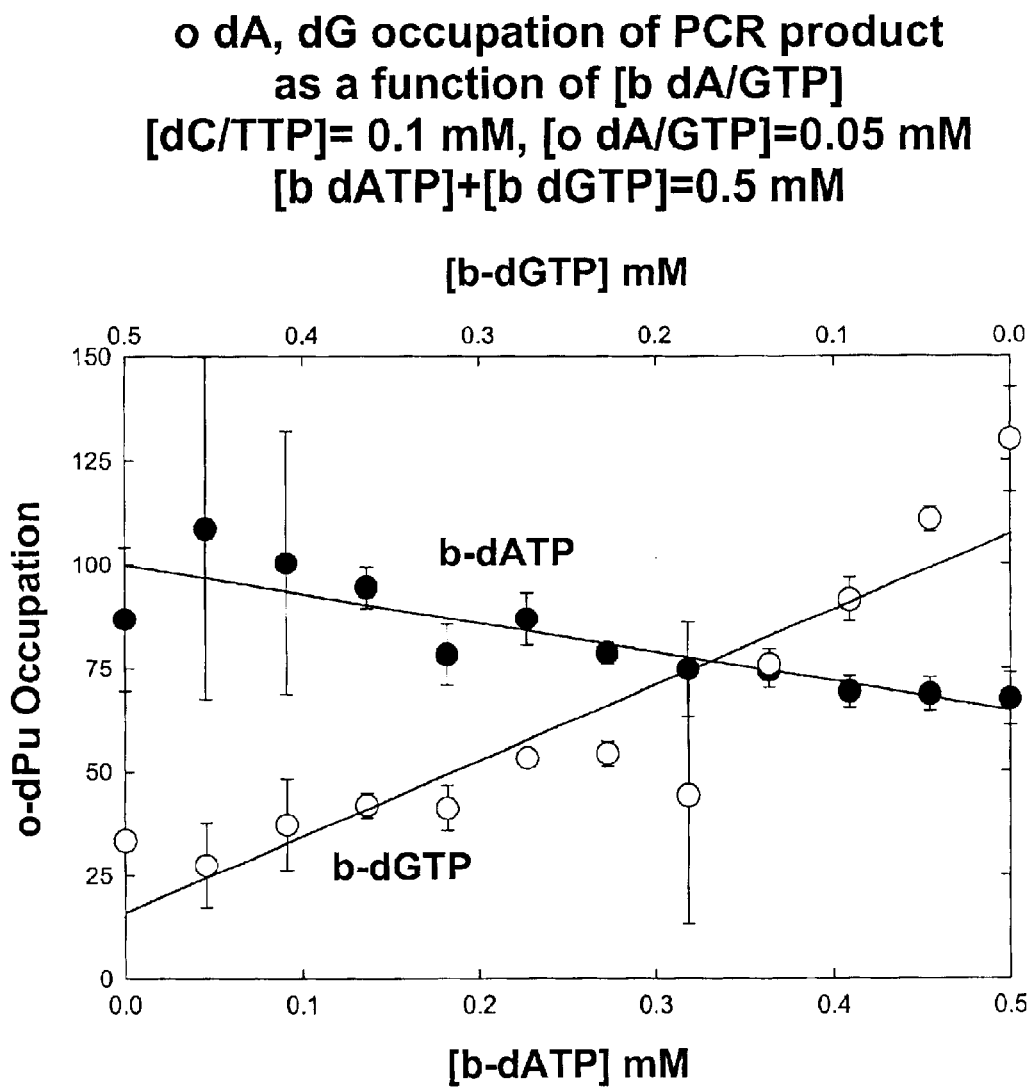
FIG. 10 is a graph PCR illustrating dPu occupation as a function of alpha boranophosphano dATP (bdATP) and alpha boranophosphano dGTP (bdGTP) concentration utilized in a PCR to optimize modified dNTP incorporation.
Figure 11:
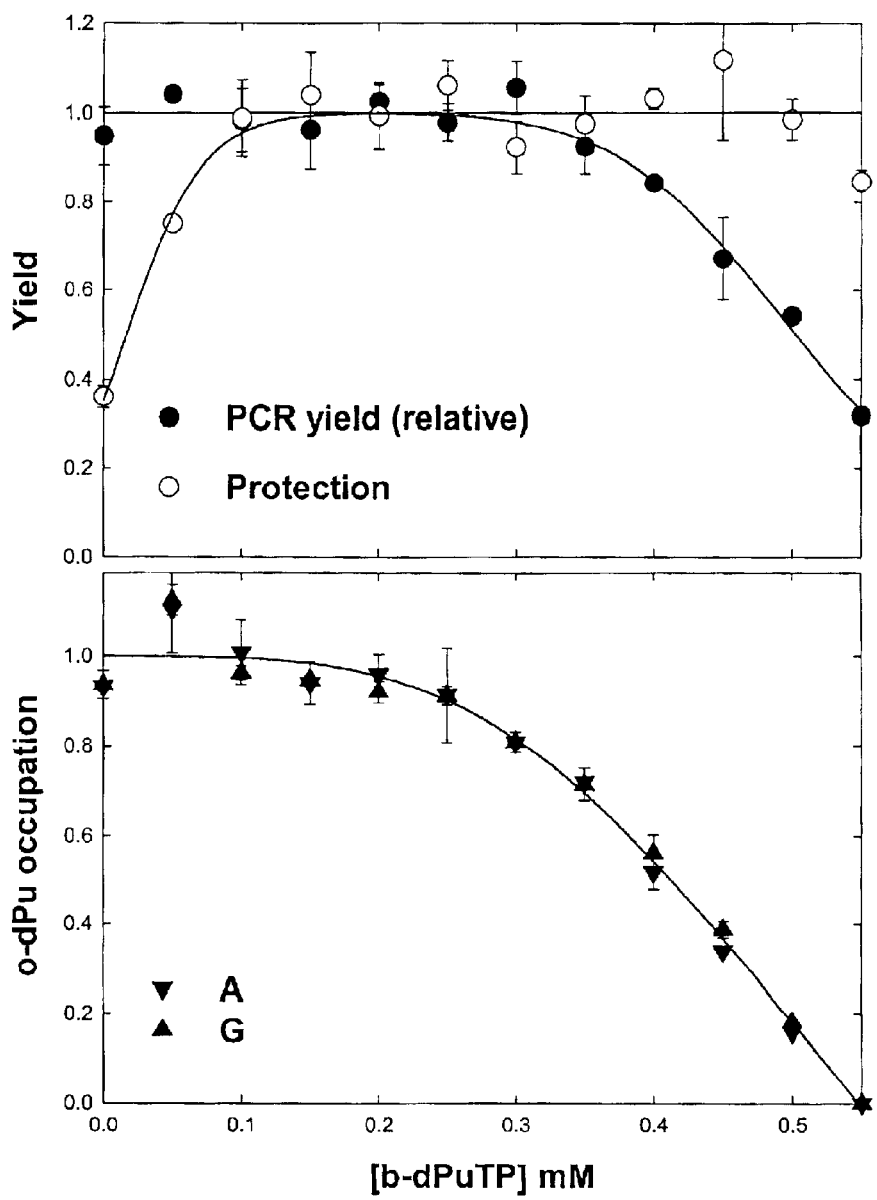
FIG. 11 contains graphs illustrating verification of the optimal bdATP/bdGTP ratio (bottom panel) established in FIG. 10. The useful (high protection levels) and unimpeding (little or no effect on PCR yield) concentration of bdPuTP range from approximately 0.1 to 0.3 mM bdPuTP (top panel).

FIG. 9 contains titration results for the four phosphoroboranes (bdNTP, N=A, C, G, T). These data show that PCR yields are negatively impacted by phosphoroboranes in the order G<A<C<T and that ExoIII protection increases in the order G>A>C≈T. These results indicate that bdPyTPs were incorporated inefficiently and the insensitivity of PCR yield to bdPyTP concentration may be largely a result of dPyTP dilution, i.e., that bdPyTPs are not particularly inhibitory. As with the thionucleotides, it is evident that Taq polymerase prefers bdPuTPs and that in keeping with a 0.8 mM total nucleotide triphosphate concentration, there would again be little room to include all bdNTPs in a reaction mix. A reasonable compromise again would be to formulate a mix that contains dNTP+bdPuTP at a total of 0.8 mM. As with the thiophosphates, this is not a requirement if one is willing to investigate the affect other nucleotide formulations have on free magnesium concentration and hence PCR performance. FIGS. 10 and 11 contain bdATP/bdGTP and dPuTP/ bdPuTP optimization results respectively. PCR was performed using lambda control primers (Perkin Elmer) and lambda DNA (Sigma) as template. All reagents (1×PCR buffer, 0.05 u/µl Taq DNA polymerase) with the exception of the nucleotide composition were from Sigma and used without modification. Cycling conditions were 94° C./30 sec., 68° C./30 sec., 72° C./60 sec for 30 cycles. The optimal bdATP/bdGTP ratio is 2.5 and verified by the overlapping data in the lower panel of FIG. 11. The useful (high protection levels) and un-impeding (little or no effect on PCR yield) concentrations of bdPuTP range from approximately 0.1 to 0.3 mM bdPuTP. The mean 5' overhangs at these concentrations are 81 and 4 bases respectively. From these data it is clear that a nucleotide mix could be formulated using bdNTPs.

Example 5

Directional Cloning of a PCR Product into a Vector

The present example is provided to demonstrate the exonuclease recession technique for providing directional cloning of a PCR product into a vector. The clonability of amplicons prepared using the above described nucleotide formulations and ExoIII digestion were compared with amplicons cloned using restriction enzyme generation of the cohesive ends. Until this point, amplification had been indiscriminately performed using Taq or REDTaq DNA polymerases. Accutaq LA and REDTaq were used for the below experiments. For integrity, Exoclone vs. restriction enzyme cloning was compared. Thus, the lambda 500 mer was amplified using primer set BamHI 1 (SEQ ID NO: 1) and XbaI 1 (SEQ ID NO: 2) for Exoclone, and a primer set designed for digestion with BamHI/XbaI (BamHI 2: cut BamHI 1 lam 5' GCACG GGATCC GAT GAG TTC GTG TCC GTA CAA CTG (SEQ ID NO: 3), XbaI 2: cut XbaI 1 lam 5' GCACG TCTAGA GGT TAT CGA AAT CAG CCA CAG CGC (SEQ ID NO: 4), recognition site underlined). After PCR the amplicons were respectively digested with ExoIII, BamHI/XbaI, ligated with BamHI/XbaI cut pUC19 and transformed into competent E. coli DH5a (Life Technologies). PCR was performed using above described primers and lambda DNA (Sigma) as template. All reagents (1×PCR buffer, 0.05 u/µl Taq DNA polymerase) with the exception of the nucleotide composition were from Sigma and used without modification. Cycling conditions were 94° C./30 sec., 68° C./30 sec., 72° C./60 sec for 30 cycles. Restriction digestion was performed using successive digestions by the restriction enzymes using a silica bind and elute DNA purification method (Qiagen PCR purification kit) between and after digestions. Ligation was at 16° C. for two hours using reagents from a ligation kit (Sigma).

Figure 12:
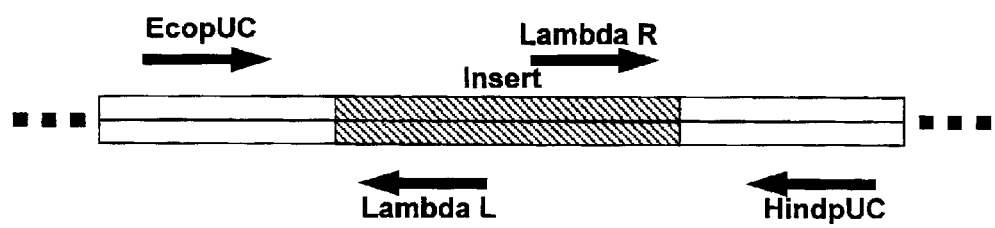
FIG. 12 is a diagram illustrating the primer possibilities utilized to confirm the directional cloning results.
Figure 12:
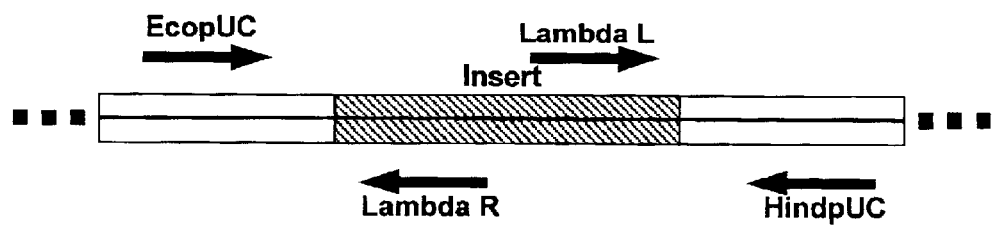
Figure 13A:
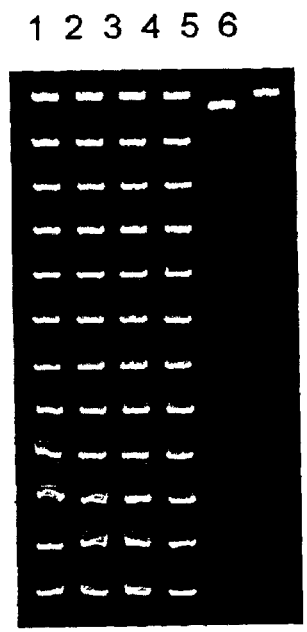
FIG. 13A is a photograph of a DNA agarose gel illustrating that amplification across the insert yielded amplicons that were larger than from pUC19 and the same as an amplification product from a previously prepared construct containing an identical insert (lanes 1–4 vs. 5 and 6 respectively).
Figure 13B:
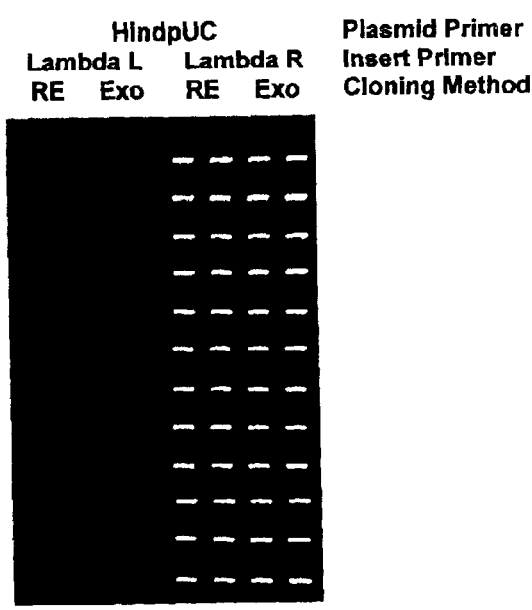
FIG. 13B are photographs of agarose gels which demonstrate that the use of primer set EcopUC/Lambda R and HindpUC/Lambda L (FIG. 12) produced no PCR products while primer sets EcopUC/LambdaL and HindpUC/Lambda R did, thus demonstrating that all of the clones produced using EcopUC/LambdaL and HindpUC/Lambda R were directionally inserted.
Figure 14:
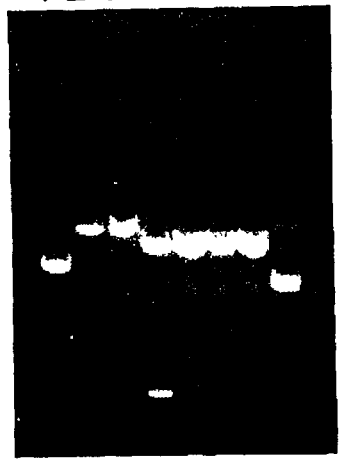
FIG. 14 is a photograph of a DNA agarose gel illustrating the expected "insert" restriction fragment generated by digesting pBX with BamHI/XbaI.

The plasmids were isolated and subjected to PCR across the inserts. Amplification across the insert (primer set EcopUC (SEQ ID NO: 5)/HindpUC (SEQ ID NO: 6), FIG. 12) yielded amplicons that were larger than from pUC19 and the same as an amplification product from a previously prepared construct containing an identical insert (FIG. 13A lanes 1–4 vs. 5 and 6 respectively). FIG. 13B demonstrates that all of the clones were directional. That is, primer pairs EcopUC (SEQ ID NO: 5)/Lambda R (SEQ ID NO: 8) and HindpUC (SEQ ID NO: 6)/Lambda L (SEQ ID NO: 7) produced no PCR products while primer pairs EcopUC (SEQ ID NO: 5)/Lambda L (SEQ ID NO: 7) and HindpUC (SEQ ID NO: 6)/Lambda R (SEQ ID NO: 8) produced PCR products. For additional evidence, one of the RE clones (pBX) was cut using BamHI, XbaI and BamHI/XbaI (FIG. 14). The double digest yielded the expected "insert" restriction fragment (FIG. 14 lane 4). The singly cut plasmid had a higher electrophoretic mobility than did singly cut pUC19 (compare FIG. 14 lanes 1,3 vs. 4,5). Removal of the insert by double digestion resulted in a fragment that comigrated with cut pUC19 (lane 4 vs. 5–7).

Example 6

Phosphoborano Modified Nucleotides vs. Phosphorothioate Modified Nucleotides

Figure 15:
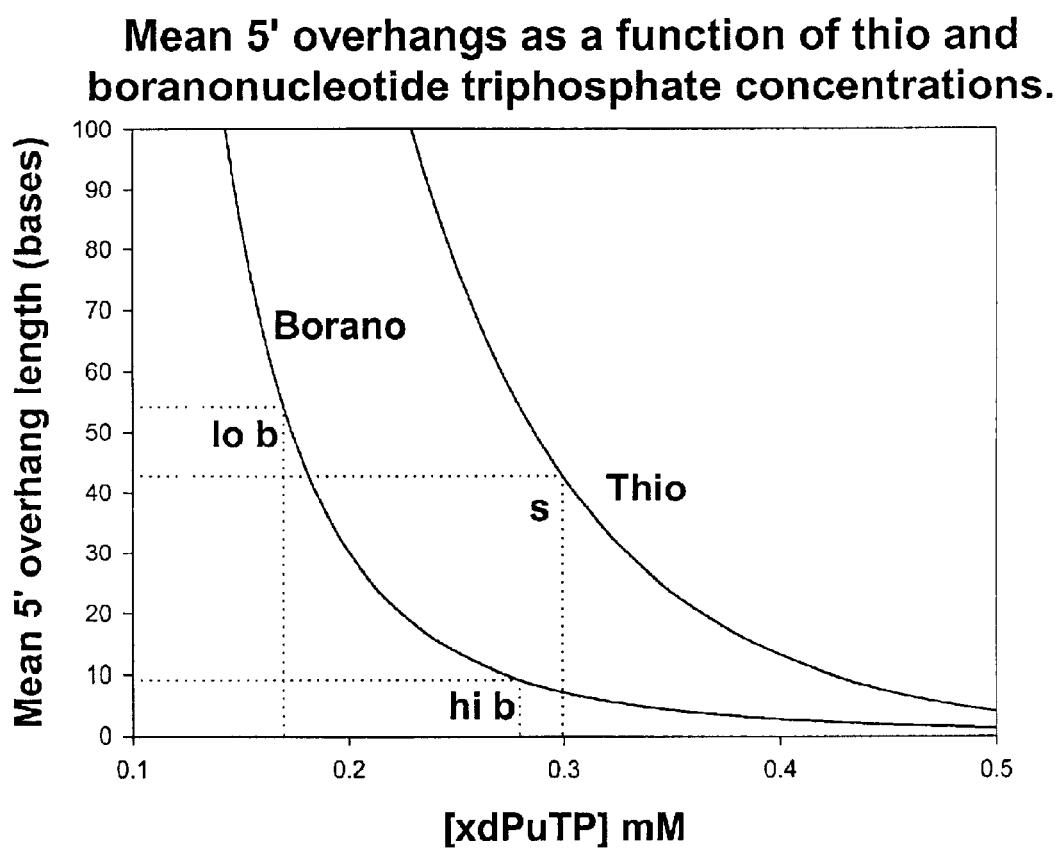
FIG. 15 is a graph illustrating the expected overhang length as a function of modified nucleotide concentration. Clearly, phosphoborano nucleotides can be used at higher cooccupation rates without impacting PCR performance.

This experiment was conducted in order to determine whether any difference in cloning exists between the use of a mixture containing phosphoborano modified nucleotides and a mixture containing phosphorothioate modified nucleotides. FIG. 15 demonstrates the expected overhang length as a function of modified nucleotide concentration. Clearly, phosphoborano nucleotides can be used at higher occupation rates with out impacting PCR performance.

Figure 16:
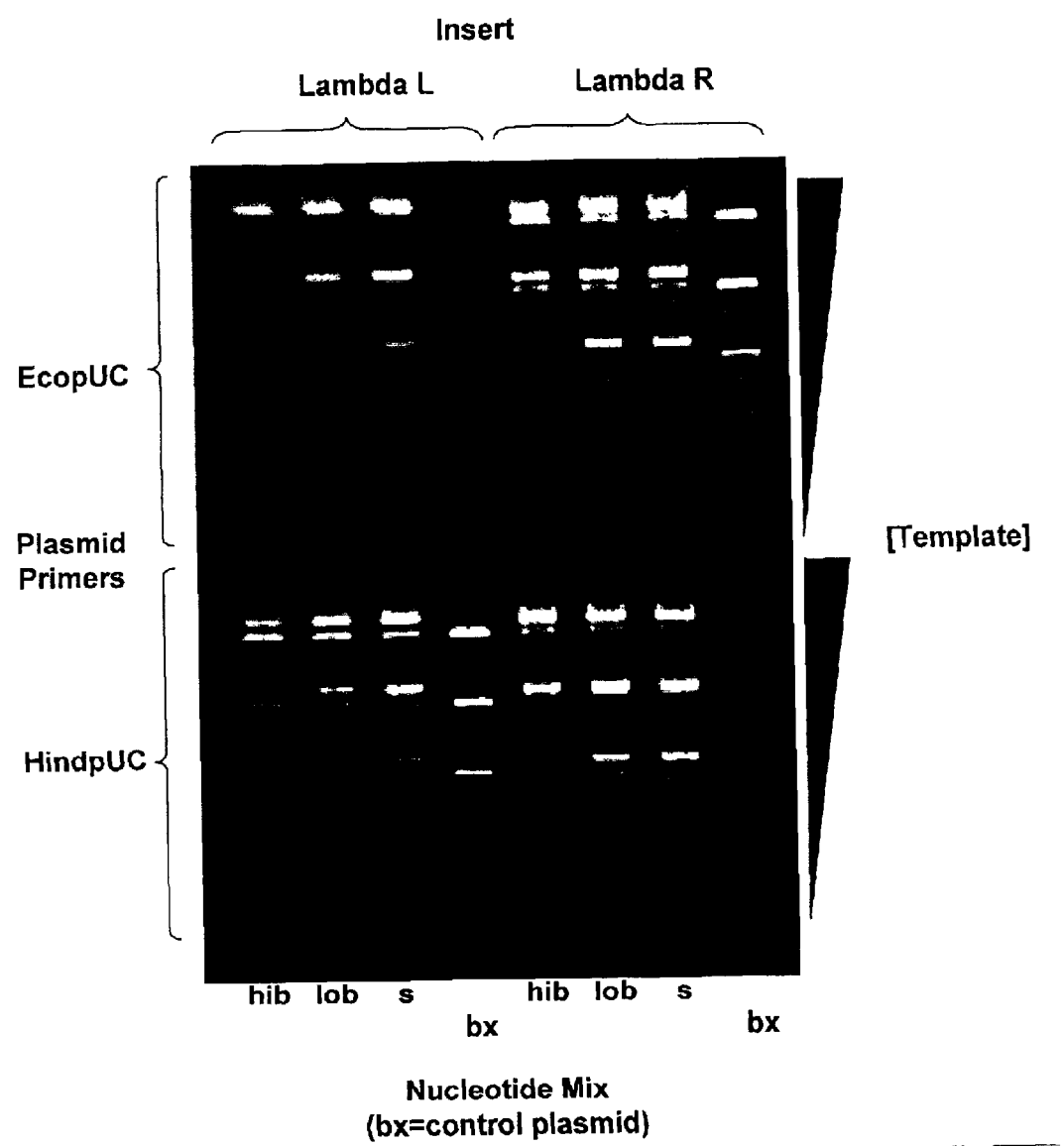
FIG. 16 is a photograph of a DNA agarose gel illustrating the resulting ligation product PCR results. All ligation reactions produced a relatively high molecular weight PCR product while only EcopUC/lambda L and HindpUC/lambda R produced products that co-migrated with the authentic clone amplification products.

Applicants then determined whether there was some advantage to ligating DNAs with shorter rather than longer 5' overhangs. For this PCR reactions (template=lambda DNA, primer set=BamHI 1 (SEQ ID NO: 1)/XbaI 1 (SEQ ID NO: 2)) at two bdPuTP and one sdPuTP (FIG. 15) concentration were ligated after exoIII digestion to BamHI/XbaI cut pUC19. PCR was performed using above described primers and lambda DNA (Sigma) as template. All reagents (1×PCR buffer, 0.05 u/µl Taq DNA polymerase) with the exception of the nucleotide composition were from Sigma and used without modification. Cycling conditions were 94° C./30 sec., 68° C./30 sec., 72° C./60 sec for 30 cycles. Ligation reactions were serially diluted 10× to obtain relative ligation efficiencies from the PCRs. FIG. 16 shows resulting PCR products. Ligation was at 16° C. for two hours using reagents from a ligation kit (Sigma). Lanes marked bx were parallel PCR performed with an authentic clone. All ligation reactions produced a relatively high molecular weight PCR product while only EcopUC/lambda L and HindpUC/lambda R produced products that co-migrated with the authentic clone amplification products. The high molecular weight products are likely amplification of dimerized insert. Relative ligation efficiencies were estimated by quantifying the bands from FIG. 16 using a BioRad gel doc image analysis system.

Example 7

Preponderance or Lack Thereof of Mutations at Single Strand Overhangs

Transformations using plasmids that potentially contain relatively long tracts of single strand sequence is non-typical. In all likelihood, cellular polymerases would repair the single stranded "lesion" making the inserted DNA entirely duplex. It is however not inconceivable that cellular repair enzymes could react unexpectedly and introduce unwanted mutations in the "lesion" region.

To investigate the cellular response fidelity, bacterial Alkaline Phosphatase (SEQ ID NO: 8) was PCR amplified from a gene bearing plasmid and cloned in E. coli (Nova Blue). Amplification was performed using the thionucleotide mix described in Example 3. 96 clones were sequenced using fluorescent cycle sequencing kit (Applied Biosystems) and analyzed for mutations as a function of mutation position vs. duplex probability. The results are shown in Table 4.

TABLE 4

Base position and fraction duplex at mutation sites

| Base Position | Fraction Duplex | Number of mutations |
|---|---|---|
| 23 | 0.579477 | 1 |
| 24 | 0.579477 | 1 |
| 29 | 0.604708 | 1 |
| 34 | 0.65072 | 1 |
| 55 | 0.82316 | 1 |
| 137 | 0.987638 | 2 |
| 158 | 0.993342 | 1 |
| 198 | 0.997814 | 1 |
| 207 | 0.998068 | 1 |
| 209 | 0.998184 | 4 |
| 214 | 0.998492 | 2 |
| 215 | 0.998582 | 1 |
| 234 | 0.999188 | 1 |
| 241 | 0.999404 | 1 |
| 248 | 0.999505 | 1 |
| 250 | 0.999535 | 2 |
| 260 | 0.999679 | 2 |
| 262 | 0.999698 | 1 |
| 297 | 0.999865 | 1 |
| 302 | 0.999895 | 1 |
| 304 | 0.999895 | 2 |
| 309 | 0.999912 | 2 |

Figure 17:
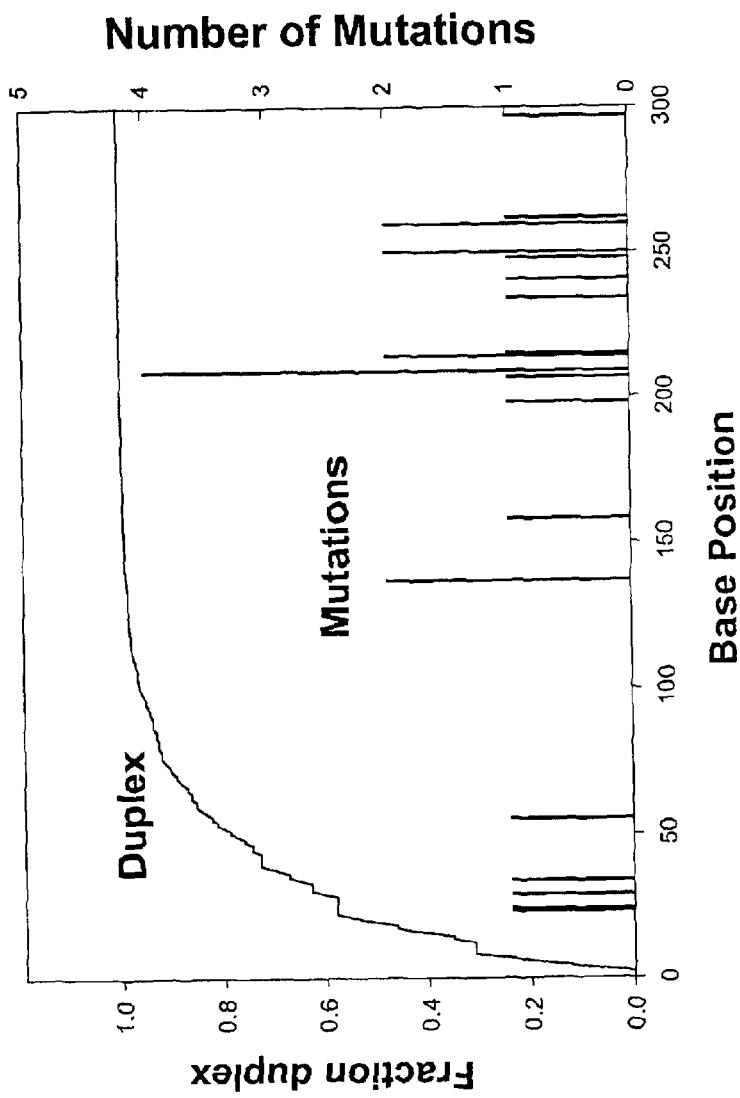
FIG. 17 is a graph illustrating the fraction duplex and the frequency of mutation as a function of sequence position. This graph demonstrates that there is no correlation between mutational frequency and degree of single stranded overhang.

The fraction (probability) duplex at each position was calculated for each position according to the probability of a base position containing 97% dATP, 100% dCTP, 97% dGTP and 100% dTTP. FIG. 17 ("duplex" curve, left axis) shows the fraction duplex and the frequency of mutation as a function of sequence position. It is clear that no correlation exists between mutational frequency and degree of single stranded overhang. As shown in the Table 4, there were no mutations found in regions of highest single stranded probability (i.e. duplex probabilities <50%) and the preponderance of mutations occurred at sites that have virtually no probability of being single stranded (i.e. duplex probability is approximately 1).

From this data, it is clear that cloning DNA containing significant lengths of single stranded overhang introduces no increased opportunity for sequence mutation.

Example 8

Generation of an Expression Library

The fact that exposure of amplicon cohesive bases is amplicon sequence independent lends this method to generation of expression libraries. 96 gene targets from E. coli were cloned using the methods described herein. 89 successful PCR reactions generated 70 clones displaying 95% or greater sequence homology with the target gene sequence. This corresponds to an approximately 80% success rate neglecting PCR failure, i.e., PCR failure can be due to many factors (primer design, cycling conditions, solution formulation and etc.) outside of the scope of the current invention. Such a success rate suggests that reliably generating expression libraries using the current processes disclosed herein is feasible.

Example 9

Self Ligation

Figure 18:
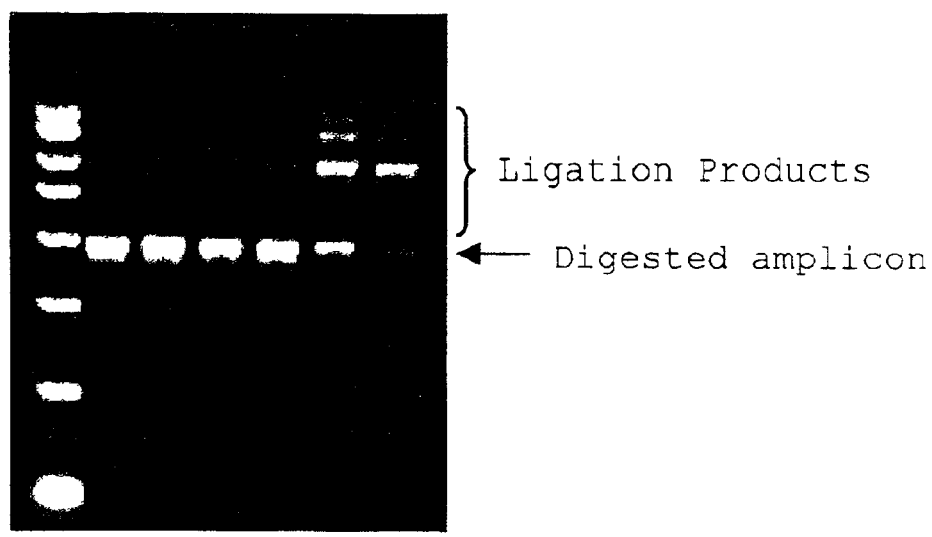
FIG. 18 is a photograph of an agarose gel which demonstrates that the the exonuclease digested amplicons are self-ligatable. The restriction enzyme fragment is an EcopUC/HindpUC amplified from pUC19 (i.e., amplified across MCS), cut with BamHI (lane B), EcoRI (lane E), HindIII (lane H), or SAlI (lane S), XbaI (lane X). Lane U is the fragment which was not digested with ExoIII.

As demonstrated in FIG. 18, the exonuclease digested amplicons are self-ligatable.

A 500 base pair fragment was amplified from lambda 500 mer DNA using a dNTP mixture containing s dATP and s dGTP, and primers specific for BamHI (lane B), EcoRI (lane E), HindIII (lane H), SalI (lane S), XbaI (lane X). The amplicon was digested with ExoIII and followed by ligation at 16° C. for 1 hour. Lane U contains an amplified fragment which was not cut with exonuclease III. As shown, all digested amplicons produced ligation products demonstrating the premise of self-ligation.

Self ligation would be helpful if one were to attempt to use this methodology in a gene shuffling or similar combinatorial/molecular evolution experiment. That is, one could take a variety of sequences, do nick translation or random priming using the dNTP mixture containing modified dNTPs, digest with exonucleaseIII then ligate to an adaptor. It is anticipated that some of the sequences express an enzyme/protein with an altered (improved) property.

Example 10

Ligation of Amplicons to Specifically Designed Adaptor Sequences

Figure 19:
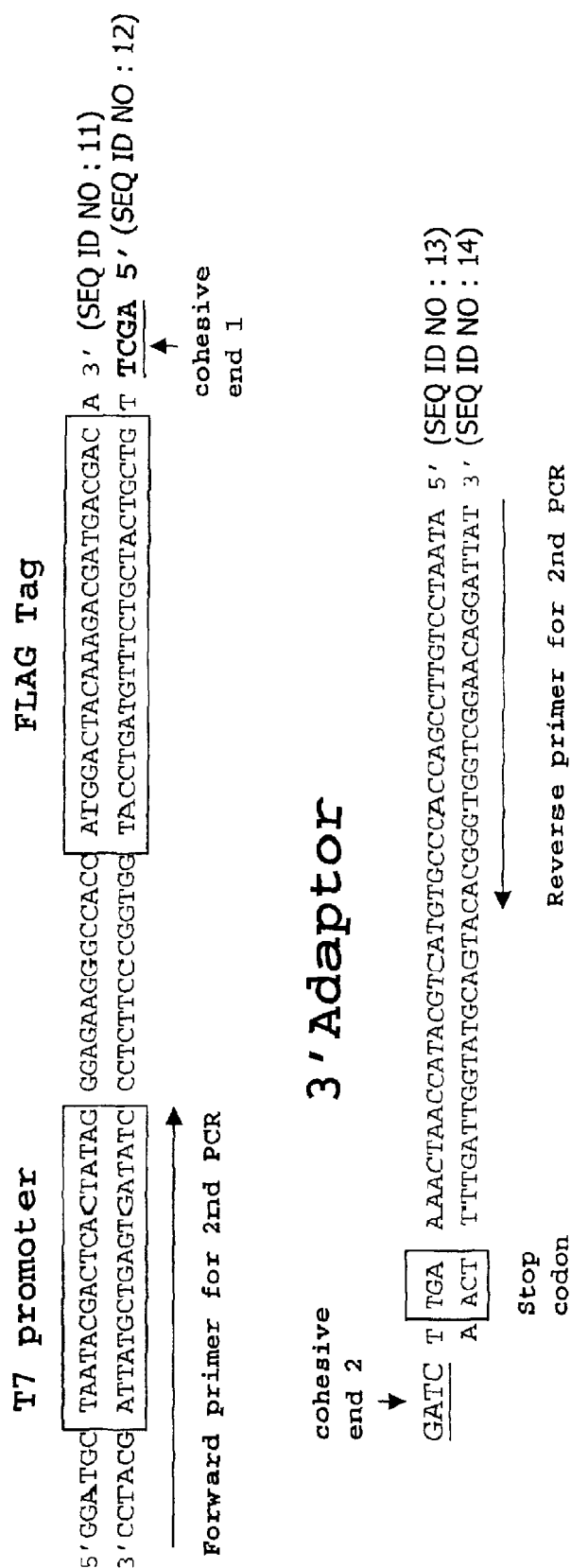
FIG. 19 illustrates the nucleotide sequences for the adaptor sequences for making linear DNA in vitro transcription/translation constructs.

FIG. 19 outlines the design of adapters designed to add attributes for in vitro translation experiment. Specifically, a 5' adapter nucleic acid was designed to contain the T7 promoter and a FLAG® octapeptide coding sequence. The stop codon was engineered into the 3' adapter. Since there is a sense strandedness to the design, i.e., ligation of an amplicon to the adapters orient with the 5' adapter upstream of a genes sense strand and the stop codon 3' of the gene's sense strand, ligation to a gene followed by amplification of the ligation product using adapter based amplification primers would be most efficient if the ligation proceeded directionally. Cohesive ends one and two were engineered into the 5' and 3' adapters respectively for this purpose. Six clones of these constructs were sequenced to corroborate that the constructs were assembled as expected. In each case the ligation orientation was shown to be as expected and without error.

Figure 20:
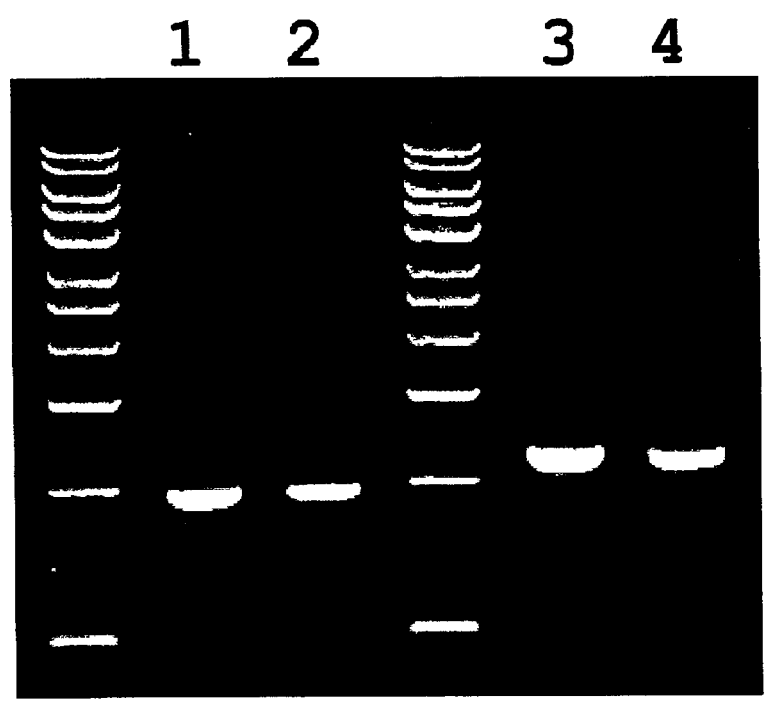
FIG. 20 is a photograph of an agarose gel which demonstrates the detection of ligation between PCR amplicon and adaptors. Lane 1 and 2 are exonuclease III treated PCR products for gene p53 and IkB, respectively. Lane 3 and 4 contain amplicons from ligated p53-adaptor and IkB-adaptor constructs using primers specific for the adaptor region.

FIG. 20 shows amplification products before (lanes 1,2) and after (lanes 3,4) ligation of the above adapter sequence to the digested amplicons (prepared by s-dATP/s-dGTP containing amplification mixture followed by ExoIII digestion) of genes p53 and IkB, respectively. Amplification of the ligation mixture using adapter specific primers clearly yielded amplicons that are longer than those obtained by amplifying with gene specific primers.

It is to be understood that the present invention has been described in detail by way of illustration and example in order to acquaint others skilled in the art with the invention, its principles, and its practical application. Further, the specific embodiments of the present invention as set forth are not intended as being exhaustive or limiting of the invention, and that many alternatives, modifications, and variations will be apparent to those skilled in the art in light of the foregoing examples and detailed description. Accordingly, this invention is intended to embrace all such alternatives, modifications, and variations that fall within the spirit and scope of the following claims. While some of the examples and descriptions above include some conclusions about the way the invention may function, the inventors do not intend to be bound by those conclusions and functions, but puts them forth only as possible explanations.

We claim:

1. A kit for directionally ligating a double-stranded nucleic acid to a first adaptor sequence, the kit comprising:
   (A) a first unmodified deoxynucleotidetriphosphate and modified deoxynucleotidetriphosphate pair, unmodified $dNTP_1$ and modified $dNTP_1$, respectively, selected from the group consisting of (1) an unmodified dATP and a modified dATP, (2) an unmodified dGTP and a modified dGTP, (3) an unmodified dCTP and a modified dCTP, (4) an unmodified dTTP and a modified dTTP, and (5) an unmodified dUTP and a modified UTP;
   (B) a second unmodified deoxynucleotidetriphosphate and modified deoxynucleotidetriphosphate pair, unmodified $dNTP_2$ and modified $dNTP_2$, respectively, selected from the group consisting of (1) an unmodified dATP and the modified dATP, (2) an unmodified dGTP and a modified dGTP, (3) an unmodified dCTP and a modified dCTP, (4) an unmodified dTTP and a modified dTTP, and (5) an unmodified dUTP and a modified UTP, wherein said first and second pairs are different; and
   (C) instructions for using the deoxynucleotidetriphosphate mixture in a procedure for directionally ligating a nucleic acid into a first adaptor sequence, wherein the adaptor sequence is a duplex nucleotide sequence for cohesive ligation to an end of an exonuclease digested amplification product;
   wherein (1) said first and second pairs are different, (2) the ratio of the modified $dNTP_1$ to the modified $dNTP_2$ relative to the unmodified $dNTP_1$ to the unmodified $dNTP_2$ is less than 51; (3) the unmodified dATP is selected from the group consisting of dATP and analogs thereof, the unmodified dGTP is selected from the group consisting of dGTP and analogs thereof, the unmodified dCTP is selected from the group consisting of dCTP and analogs thereof, the unmodified dTTP is selected from the group consisting of dTTP and analogs thereof, and the unmodified dUTP is selected from the group consisting of dUTP and analogs thereof, (4) the analogs of dATP, dGTP, dCTP, dTTP, and dUTP do not impart resistance against enzymatic degradation by an exonuclease relative to dATP, dGTP, dCTP, dTTP, and dUTP, respectively, when incorporated into a polynucleotide, and (5) the modified dATP, modified dGTP, modified dCTP, modified dTTP, or modified dUTP when incorporated into a polynucleotide imparts resistance, relative to dATP, dGTP, dCTP, dTTP, and dUTP, respectively, against enzymatic degradation by an exonuclease at the site of incorporation.

2. The kit of claim 1 wherein the ratio of the modified $dNTP_1$ to the modified $dNTP_2$ relative to the unmodified $dNTP_1$ to the unmodified $dNTP_2$ is less than 27.

3. The kit of claim 2 wherein the ratio of the modified $dNTP_1$ to the modified $dNTP_2$ relative to the unmodified $dNTP_1$ to the unmodified $dNTP_2$ is less than 13.

4. The kit of claim 1 wherein the modified $dNTP_1$ and the modified $dNTP_2$ are alpha phosphate substituted deoxynucleotidetriphosphates.

5. The kit of claim 4 wherein the ratio of the modified $dNTP_1$ to the modified $dNTP_2$ relative to the unmodified $dNTP_1$ to the unmodified $dNTP_2$ is between about 0.05 and 6.4.

6. The kit of claim 5 wherein the ratio of the modified $dNTP_1$ to the modified $dNTP_2$ relative to the unmodified $dNTP_1$ to the unmodified $dNTP_2$ is between about 0.1 and 3.2.

7. The kit of claim 6 wherein the ratio of the modified $dNTP_1$ to the modified $dNTP_2$ relative to the unmodified $dNTP_1$ to the unmodified $dNTP_2$ is between about 0.2 and 1.6.

8. The kit of claim 5 wherein the unmodified $dNTP_1$ is the unmodified dGTP, the unmodified $dNTP_2$ is the unmodified dATP, the modified $dNTP_1$ is an alpha thiophosphorano dGTP, and the modified $dNTP_2$ is an alpha thiophosphorano dATP.

9. The kit of claim 1 wherein the modified $dNTP_1$ and the modified $dNTP_2$ are alpha thiophosphorano deoxynucleotidetriphosphates.

10. The kit of claim 9 wherein the unmodified $dNTP_1$ is the unmodified dGTP, the unmodified $dNTP_2$ is the unmodified dATP, the modified $dNTP_1$ is an alpha thiophosphorano dGTP, and the modified $dNTP_2$ is an alpha thiophosphorano dATP.

11. The kit of claim 10 wherein the ratio of the alpha thiophosphorano dGTP to the alpha thiophosphorano dATP relative to the unmodified dGTP to the unmodified dATP is between 0.8 and 5.3.

12. The kit of claim 10 wherein the ratio of the alpha thiophosphorano dGTP to the alpha thiophosphorano dATP relative to the unmodified dGTP to the unmodified dATP is between 0.17 and 2.7.

13. The kit of claim 12 wherein the ratio of the alpha thiophosphorano dGTP to the alpha thiophosphorano dATP relative to the unmodified dGTP to the unmodified dATP is between 0.33 and 1.33.

14. The kit of claim 13 wherein the ratio of the alpha thiophosphorano dGTP to the alpha thiophosphorano dATP relative to the unmodified dGTP to the unmodified dATP is about 0.66.

15. The kit of claim 1 wherein the modified $dNTP_1$ and the modified $dNTP_2$ are alpha boranophosphorano deoxynucleotidetriphosphates.

16. The kit of claim 15 wherein the unmodified $dNTP_1$ is the unmodified dGTP, the unmodified $dNTP_2$ is the unmodified dATP, the modified $dNTP_1$ is an alpha boranophosphorano dGTP, and the modified $dNTP_2$ is an alpha boranophosphorano dATP.

17. The kit of claim 16 wherein the ratio of the alpha boranophosphoraflo dGTP to the alpha boranophosphorano dATP relative to the unmodified dGTP to the unmodified dATP is between 0.05 and 6.4.

18. The kit of claim 17 wherein the ratio of the alpha boranophosphorano dGTP to the alpha boranophosphorano dATP relative to the unmodified dGTP to the unmodified dATP is between 0.1 and 3.2.

19. The kit of claim 18 wherein the ratio of the alpha boranophosphorano dGTP to the alpha boranophosphorano dATP relative to the unmodified dGTP to the unmodified dATP is between 0.2 and 1.6.

20. The kit of claim 19 wherein the ratio of the alpha boranophosphorano dGTP to the alpha boranophosphorano dATP relative to the unmodified dGTP to the unmodified dATP is about 0.4.

21. A kit for directionally ligating a double-stranded nucleic acid to a first adaptor sequence, the kit comprising:
   (A) a deoxynucleotidetriphosphate mixture comprising:
      (1) (a) an unmodified dATP selected from the group consisting of dATP and analogs thereof, (b) an unmodified dGTP selected from the group consisting of dGTP and analogs thereof, (c) an unmodified dCTP selected from the group consisting of dCTP and analogs thereof, and (d) (i) an unmodified dTTP selected from the group consisting of dTTP and analogs thereof, or (ii) an unmodified dUTP selected from the group consisting of dUTP and analogs thereof; and (2) at least one modified deoxynucleotidetriphosphate selected from the group consisting of a modified dATP, a modified dGTP, a modified dCTP, a modified dTTP, and a modified dUTP;

(B) a first adaptor sequence, wherein the first adaptor sequence comprises a nucleotide sequence encoding at least one epitope tag; and (C) instructions for using the deoxynucleotidetriphosphate mixture in a procedure for directionally ligating a nucleic acid into the first adaptor sequence;

wherein (1) the analogs of dATP, dGTP, dCTP, dTTP, and dUTP do not impart resistance against enzymatic degradation by an exonuclease relative to dATP, dGTP, dCTP, dTTP, and dUTP, respectively, when incorporated into a polynucleotide; (2) the modified dATP, modified dGTP, modified dCTP, modified dTTP, or modified dUTP when incorporated into a polynucleotide imparts resistance, relative to dATP, dGTP, dCTP, dTTP, and dUTP, respectively, against enzymatic degradation by an exonuclease at the site of incorporation; and (3) the adaptor sequence is a duplex nucleotide sequence for cohesive ligation to an end of an exonuclease digested amplification product.

22. The kit of claim 21 wherein the first adaptor sequence comprises an epitope tag selected from the group consisting of c-myc, polyhistidine, polyarginine, glutathione-S-transferase (GST) tag, HA epitope, V5, and DYKDDDDK.

23. The kit of claim 22 wherein the first adaptor sequence comprises a DYKDDDDK epitope tag.

24. The kit of claim 21 further comprising a second adaptor sequence.

25. The kit of claim 24 wherein the second adaptor sequence comprises a nucleotide sequence encoding at least one epitope tag and the epitope tag comprises c-myc, polyhistidine, polyarginine, glutathione-S-transferase (GST) tag, HA epitope, V5, or sequence DYKDDDDK.

26. The kit of claim 25 wherein at least one epitope tag of the second adaptor sequence comprises the sequence DYKDDDDK.

27. A kit for directionally ligating a double-stranded nucleic acid to a first adaptor sequence, the kit comprising:

(A) a deoxynucleotidetriphosphate mixture comprising:

(1) (a) an unmodified dATP selected from the group consisting of dATP and analogs thereof, (b) an unmodified dGTP selected from the group consisting of dGTP and analogs thereof, (c) an unmodified dCTP selected from the group consisting of dCTP and analogs thereof, and (d) (i) an unmodified dTTP selected from the group consisting of dTTP and analogs thereof, or (ii) an unmodified dUTP selected from the group consisting of dUTP and analogs thereof; and (2) at least one modified deoxynucleotidetriphosphate selected from the group consisting of a modified dATP, a modified dGTP, a modified dCTP, a modified dTTP, and a modified dUTP;

(B) a first primer and a second primer; and (C) instructions for using the deoxynucleotidetriphosphate mixture in a procedure for directionally ligating a nucleic acid into a first adaptor sequence;

wherein (1) the analogs of dATP, dGTP, dCTP, dTTP, and dUTP do not impart resistance against enzymatic degradation by an exonuclease relative to dATP, dGTP, dCTP, dTTP, and dUTP, respectively, when incorporated into a polynucleotide; (2) the modified dATP, modified dGTP, modified dCTP, modified dTTP, or modified dUTP when incorporated into a polynucleotide imparts resistance, relative to dATP, dGTP, dCTP, dTTP, and dUTP, respectively, against enzymatic degradation by an exonuclease at the site of incorporation; (3) the first primer is complimentary to a first strand of the double-stranded nucleic acid, and has a first terminus complimentary to a first ligation site sequence of the first adaptor sequence; (4) the second primer is complimentary to a second strand of the double-stranded nucleic acid and has a second terminus complimentary to a second ligation site sequence of a second adaptor sequence; (5) the first terminus of the first primer and the second terminus of the second primer are not identical; and (6) each adaptor sequence is a duplex nucleotide sequence for cohesive ligation to an end of an exonuclease digested amplification product.

28. The kit of claim 27 wherein the first terminus or the second terminus is about one to about ten nucleotides in length.

29. The kit of claim 28 wherein the first terminus or the second terminus is two to seven nucleotides in length.

30. The kit of claim 29 wherein the first terminus or the second terminus is two to five nucleotides in length.

31. The kit of claim 30 wherein the first terminus or the second terminus is four nucleotides in length.

32. The kit of claim 27 wherein the first terminus is a 3' terminus and the second terminus is a 3' terminus.

33. The kit of claim 27 wherein the first terminus is a 5' terminus and the second terminus is a 5' terminus.

34. The kit of claim 33 wherein the first terminus is four nucleotides in length, the second terminus is four nucleotides in length, and the first terminus and the second terminus are not identical.

35. The kit of claim 27 further comprising instructions for using the deoxynucleotidetriphosphate mixture in a procedure for directionally ligating the nucleic acid into a second adaptor sequence.

36. A deoxynucleotidetriphosphate mixture comprising:

(A) (1) an unmodified dATP selected from the group consisting of dATP and analogs thereof, (2) an unmodified dGTP selected from the group consisting of dGTP and analogs thereof, (3) an unmodified dCTP selected from the group consisting of dCTP and analogs thereof, and (4) (a) an unmodified dTTP selected from the group consisting of dTTP and analogs thereof, or (b) an unmodified dUTP selected from the group consisting of dUTP and analogs thereof and (B) at least two modified deoxynucleotidetriphosphates selected from the group consisting of a modified dATP, a modified dGTP, a modified dCTP, a modified dTTP, and a modified dUTP;

wherein (1) the analogs of dATP, dGTP, dCTP, dTTP, and dUTP do not impart resistance against enzymatic degradation by an exonuclease relative to dATP, dGTP, dCTP, dTTP, and dUTP, respectively, when incorporated into a polynucleotide; and (2) the modified dATP, modified dGTP, modified dCTP, modified dTTP, or modified dUTP when incorporated into a polynucleotide imparts resistance, relative to dATP, dGTP, dCTP, dTTP, and dUTP, respectively, against enzymatic degradation by an exonuclease at the site of incorporation.

37. The dNTP mixture of claim 36 wherein the mixture comprises:
  (A) a first unmodified deoxynucleotidetriphosphate and modified deoxynucleotidetriphosphate pair, unmodified $dNTP_1$ and modified $dNTP_1$, respectively, selected from the group consisting of (1) the unmodified dATP and the modified dATP, (2) the unmodified dGTP and the modified dGTP, (3) the unmodified dCTP and the modified dCTP, (4) the unmodified dTTP and the modified dTTP, and (5) the unmodified dUTP and the modified UTP; and
  (B) a second unmodified deoxynucleotidetriphosphate and modified deoxynucleotidetriphosphate pair, unmodified $dNTP_2$ and modified $dNTP_2$, respectively, selected from the group consisting of (1) the unmodified dATP and the modified dATP, (2) the unmodified dGTP and the modified dGTP, (3) the unmodified dCTP and the modified dCTP, (4) the unmodified dTTP and the modified dTTP, and (5) the unmodified dUTP and the modified UTP;
  wherein said first and second pairs are different; and the ratio of the modified $dNTP_1$ to the modified $dNTP_2$ relative to the unmodified $dNTP_1$ to the unmodified $dNTP_2$ is less than 51.

38. The mixture of claim 37 wherein the ratio of the modified $dNTP_1$ to the modified $dNTP_2$ relative to the unmodified $dNTP_1$ to the unmodified $dNTP_2$ is less than 27.

39. The mixture of claim 38 wherein the ratio of the modified $dNTP_1$ to the modified $dNTP_2$ relative to the unmodified $dNTP_1$ to the unmodified $dNTP_2$ is less than 13.

40. The mixture of claim 37 wherein the modified $dNTP_1$ and the modified $dNTP_2$ are alpha phosphate substituted deoxynucleotidetriphosphates.

41. The mixture of claim 40 wherein the ratio of the alpha phosphate substituted $dNTP_1$ to the alpha phosphate substituted $dNTP_2$ relative to the unmodified $dNTP_1$ to the unmodified $dNTP_2$ is between 0.05 and 6.4.

42. The mixture of claim 41 wherein the ratio of the alpha phosphate substituted $dNTP_1$ to the alpha phosphate substituted $dNTP_2$ relative to the unmodified $dNTP_1$ to the unmodified $dNTP_2$ is between 0.1 and 3.2.

43. The mixture of claim 42 wherein the ratio of the alpha phosphate substituted $dNTP_1$ to the alpha phosphate substituted $dNTP_2$ relative to the unmodified $dNTP_1$ to the unmodified $dNTP_2$ is between 0.2 and 1.6.

44. The mixture of claim 41 wherein the unmodified $dNTP_1$ is the unmodified dGTP, the unmodified $dNTP_2$ is the unmodified dATP, the modified $dNTP_1$ is an alpha thiophosphorano dGTP, and the modified $dNTP_2$ is an alpha thiophosphorano dATP.

45. The mixture of claim 40 wherein the modified $dNTP_1$ and the modified $dNTP_2$ are alpha thiophosphorano deoxynucleotidetriphosphates.

46. The mixture of claim 45 wherein the unmodified $dNTP_1$ is the unmodified dGTP, the unmodified $dNTP_2$ is the unmodified dATP, the modified $dNTP_1$ is an alpha thiophosphorano dGTP, and the modified $dNTP_2$ is an alpha thiophosphorano dATP.

47. The mixture of claim 46 wherein the ratio of the alpha thiophosphorano dGTP to the alpha thiophosphorano dATP relative to the unmodified dGTP to the unmodified dATP is between 0.8 and 5.3.

48. The mixture of claim 46 wherein the ratio of alpha thiophosphorano dGTP to the alpha thiophosphorano dATP relative to the unmodified dGTP to the unmodified dATP is between 0.17 and 2.7.

49. The mixture of claim 48 wherein the ratio of the alpha thiophosphorano dGTP to the alpha thiophosphorano dATP relative to the unmodified dGTP to the unmodified dATP is between 0.33 and 1.33.

50. The mixture of claim 49 wherein the ratio of the alpha thiophosphorano dGTP to the alpha thiophosphorano dATP relative to the unmodified dGTP to the unmodified dATP is about 0.66.

51. The mixture of claim 40 wherein the modified $dNTP_1$ and the modified $dNTP_2$ are alpha boranophosphorano deoxynucleotidetriphosphates.

52. The mixture of claim 51 wherein the unmodified $dNTP_1$ is the unmodified dGTP, the unmodified $dNTP_2$ is the unmodified dATP, the modified $dNTP_1$ is an alpha boranophosphorano dGTP, and the modified $dNTP_2$ is an alpha boranophosphorano dATP.

53. The mixture of claim 52 wherein the ratio of the alpha boranophosphorano dGTP to the alpha boranophosphorano dATP relative to the unmodified dGTP to the unmodified dATP is between 0.05 and 6.4.

54. The mixture of claim 53 wherein the ratio of the alpha boranophosphorano dGTP to the alpha boranophosphorano dATP relative to the unmodified dGTP to the unmodified dATP is between 0.1 and 3.2.

55. The mixture of claim 54 wherein the ratio of the alpha boranophosphorano dGTP to the alpha boranophosphorano dATP relative to the unmodified dGTP to the unmodified dATP is between 0.2 to 1.6.

56. The mixture of claim 55 wherein the ratio of the alpha boranophosphorano dGTP to the alpha boranophosphorano dATP relative to the unmodified dGTP to the unmodified dATP is about 0.4.

57. A kit for directionally ligating a double-stranded nucleic acid to a first adaptor sequence, the kit comprising:
  (A) a deoxynucleotidetriphosphate (dNTP) mixture, the dNTP mixture comprising modified dNTPs for at least one of the four nucleotide triphosphates comprising dATP, dGTP, dCTP, dTTP and analogs thereof, which, when incorporated into a polynucleotide, impart resistance against enzymatic degradation by an exonuclease at the site of incorporation of the modified dNTPs; and
  (B) a first adaptor sequence comprising a nucleotide sequence encoding at least one epitope tag; and
  (C) instructions for using the deoxynucleotidetriphosphate mixture in a procedure for directionally ligating a nucleic acid into a first adaptor sequence.

58. The kit of claim 57 wherein the first adaptor sequence comprises an epitope tag selected from the group consisting of c-myc, polyhistidine, polyarginine, glutathione-S-transferase (GST) tag, HA epitope, V5, and DYKDDDDK.

59. The kit of claim 58 wherein the first adaptor sequence comprises a DYKDDDDK epitope tag.

60. A kit for directionally ligating a double-stranded nucleic acid to a first adaptor sequence, the kit comprising:
  (A) a deoxynucleotidetriphosphate mixture comprising:
    (1) (a) dATP, (b) dGTP, (c) dCTP, and (d) dTTP; and
    (2) at least one modified deoxynucleotidetriphosphate selected from the group consisting of a modified dATP, a modified dGTP, a modified dCTP, a modified dTTP, and a modified dUTP wherein the modified dATP, modified dGTP, modified dCTP, or modified dTTP when incorporated into a polynucleotide imparts resistance, relative to dATP, dGTP, dCTP, and dTTP, respectively, against enzymatic degradation by an exonuclease at the site of incorporation;
  (B) a first primer complimentary to a first strand of the double-stranded nucleic acid, the first primer having a first terminus complimentary to a first ligation site sequence of the first adaptor sequence;

(C) a second primer complimentary to a second strand of the double-stranded nucleic acid, the second primer having a second terminus complimentary to a second ligation site sequence of a second adaptor sequence, wherein the first terminus of the first primer and the second terminus of the second primer are not identical;

(D) an exonuclease;

(E) at least one polymerase; and (F) instructions for using the deoxynucleotidetriphosphate mixture in a procedure for directionally ligating a nucleic acid into a first adaptor sequence and a second adaptor sequence, wherein the adaptor sequences are duplex nucleotide sequences for cohesive ligation to an end of an exonuclease digested amplification product.

61. The kit of claim 60 further comprising:

(G) the first adaptor sequence, wherein the first adaptor sequence comprises a DYKDDDDK epitope tag; and (H) the second adaptor sequence.

62. The kit of claim 61 wherein the modified deoxynucleotidetriphosphates consist of an alpha thiophosphorano dGTP and an alpha thiophosphorano dATP.

63. The kit of claim 62 wherein the first primer has a 5' terminus and the second primer has a 5' terminus.

64. The kit of claim 63 wherein the exonuclease is an exonuclease III.

65. The kit of claim 64 wherein at least one polymerase is a Taq polymerase or a recombinant Taq polymerase.

66. The kit of claim 65 wherein there are at least two polymerases.

* * * * *

UNITED STATES PATENT AND TRADEMARK OFFICE
CERTIFICATE OF CORRECTION

PATENT NO. : 6,902,914 B2
DATED : June 7, 2005
INVENTOR(S) : Ward et al.

It is certified that error appears in the above-identified patent and that said Letters Patent is hereby corrected as shown below:

Column 2,
Line 2, "5" should read -- 5' --.

Column 3,
Line 56, "using the an" should read -- using an --.

Column 6,
Line 55, "5" should read -- 5' --.

Column 11,
Line 64, "th" should read -- the --.

Column 19,
Line 29, "100,000" should read -- 100,000 times --.

Column 22,
Line 7, "MS" should read -- M5 --.

Column 23,
Line 29, "furthers contain" should read -- further contains --.

Column 25,
Line 56, "restrioction" should read -- restriction --.

Column 27,
Line 16, "DAMP" should read -- dAMP --.

Column 32,
Line 31, "genes" should read -- gene's --.

Column 35,
Seq. No. 10 <223>, "RECOMBINANY" should read -- RECOMBINANT --.

Column 37,
Seq. No. 11 <223>, (both occurrences) "promotoer" should read -- promoter --.

Column 39,
Lines 12 and 21, "UTP" should read -- dUTP --.
Line 17, "the" should read -- a --.

UNITED STATES PATENT AND TRADEMARK OFFICE
CERTIFICATE OF CORRECTION

PATENT NO. : 6,902,914 B2
DATED : June 7, 2005
INVENTOR(S) : Ward et al.

It is certified that error appears in the above-identified patent and that said Letters Patent is hereby corrected as shown below:

Column 42,
Line 53, "thereof" should read -- thereof; --.

Column 43,
Lines 11 and 19, "UTP" should read -- dUTP --.

Signed and Sealed this

Twenty-first Day of February, 2006

JON W. DUDAS
*Director of the United States Patent and Trademark Office*

SEQUENCE LISTING

<160> NUMBER OF SEQ ID NOS: 14

<210> SEQ ID NO 1
<211> LENGTH: 28
<212> TYPE: DNA
<213> ORGANISM: Lambda phage
<220> FEATURE:
<221> NAME/KEY: misc_feature
<222> LOCATION: (1)..(28)
<223> OTHER INFORMATION: Primer for Polymerase Chain Reaction (PCR)

<400> SEQUENCE: 1
gatcgatgag ttcgtgtccg tacaactg                                        28

<210> SEQ ID NO 2
<211> LENGTH: 28
<212> TYPE: DNA
<213> ORGANISM: Lambda phage
<220> FEATURE:
<221> NAME/KEY: misc_feature
<222> LOCATION: (1)..(28)
<223> OTHER INFORMATION: Primer for Polymerase Chain Reaction (PCR)

<400> SEQUENCE: 2
ctagggttat cgaaatcagc cacagcgc                                        28

<210> SEQ ID NO 3
<211> LENGTH: 35
<212> TYPE: DNA
<213> ORGANISM: Lambda phage
<220> FEATURE:
<221> NAME/KEY: misc_feature
<222> LOCATION: (1)..(35)
<223> OTHER INFORMATION: Primer for Polymerase Chain Reaction (PCR)

<400> SEQUENCE: 3
gcacgggatc cgatgagttc gtgtccgtac aactg                                35

<210> SEQ ID NO 4
<211> LENGTH: 35
<212> TYPE: DNA
<213> ORGANISM: Lambda phage
<220> FEATURE:
<221> NAME/KEY: misc_feature
<222> LOCATION: (1)..(35)
<223> OTHER INFORMATION: Primer for Polymerase Chain Reaction (PCR)

<400> SEQUENCE: 4
gcacgtctag aggttatcga aatcagccac agcgc                                35

<210> SEQ ID NO 5
<211> LENGTH: 23
<212> TYPE: DNA
<213> ORGANISM: Lambda phage
<220> FEATURE:
<221> NAME/KEY: misc_feature
<222> LOCATION: (1)..(23)
<223> OTHER INFORMATION: Primer for Polymerase Chain Reaction (PCR)

<400> SEQUENCE: 5
cagtcacgac gttgtaaaac gac                                             23

<210> SEQ ID NO 6
<211> LENGTH: 23
<212> TYPE: DNA
<213> ORGANISM: Lambda phage

-continued

```
<220> FEATURE:
<221> NAME/KEY: misc_feature
<222> LOCATION: (1)..(23)
<223> OTHER INFORMATION: Primer for Polymerase Chain Reaction (PCR)

<400> SEQUENCE: 6
cacaggaaac agctatgacc atg                                          23

<210> SEQ ID NO 7
<211> LENGTH: 23
<212> TYPE: DNA
<213> ORGANISM: Lambda phage
<220> FEATURE:
<221> NAME/KEY: misc_feature
<222> LOCATION: (1)..(23)
<223> OTHER INFORMATION: Primer for Polymerase Chain Reaction (PCR)

<400> SEQUENCE: 7
ggcaatcagt tcatctttcg tca                                          23

<210> SEQ ID NO 8
<211> LENGTH: 22
<212> TYPE: DNA
<213> ORGANISM: Lambda phage
<220> FEATURE:
<221> NAME/KEY: misc_feature
<222> LOCATION: (1)..(22)
<223> OTHER INFORMATION: Primer for Polymerase Chain Reaction (PCR)

<400> SEQUENCE: 8
gtgtggcagc cgaaatgaca ga                                           22

<210> SEQ ID NO 9
<211> LENGTH: 558
<212> TYPE: DNA
<213> ORGANISM: Escherichia coli

<400> SEQUENCE: 9
agcttctcga gatgcctgtt ctggaaaacc gggctgctca gggcgatatt actgcacccg    60
gcggtgctcg ccgtttaacg ggtgatcaga ctgccgctct gcgtgattct cttagcgata   120
aacctgcaaa aaatattatt ttgctgattg gcgatgggat gggggactcg gaaattactg   180
ccgcacgtaa ttatgccgaa ggtgcgggcg gcttttttaa aggtatagat gccttaccgc   240
ttaccgggca atacactcac tatgcgctga ataaaaaaac cggcaaaccg gactacgtca   300
ccgactcggc tgcatcagca accgcctggt caaccggtgt caaaacctat aacgcgcgc    360 tgggcgtcga tattcacgaa aaagatcacc caacgattct ggaaatggca aagccgcag    420 gtctggcgac cggtaacgtt tctaccgcag agttgcagga tgccacgccc gctgcgctgg   480
tggcacatgt gacctcgcgc aaatgctacg gtccgagcgc gaccagtgaa aaatgtccgg   540
gtaacgctct ggaaaaag                                                 558

<210> SEQ ID NO 10
<211> LENGTH: 8
<212> TYPE: PRT
<213> ORGANISM: Artificial Sequence
<220> FEATURE:
<223> OTHER INFORMATION: TAG USED TO PURIFY RECOMINANT PROTEIN
<220> FEATURE:
<221> NAME/KEY: BINDING
<222> LOCATION: (1)..(8)
<223> OTHER INFORMATION: TAG USED TO PURIFY RECOMBINANY PROTEIN

<400> SEQUENCE: 10
```

-continued

```
Asp Tyr Lys Asp Asp Asp Asp Lys
1               5
```

<210> SEQ ID NO 11
<211> LENGTH: 60
<212> TYPE: DNA
<213> ORGANISM: Artificial Sequence
<220> FEATURE:
<223> OTHER INFORMATION: forward primer containing T7 promotoer and FLAG
      octapeptide designed to incorporate these sequences into
      amplification products
<220> FEATURE:
<221> NAME/KEY: promoter
<222> LOCATION: (1)..(60)
<223> OTHER INFORMATION: forward primer containing T7 promotoer and FLAG
      octapeptide designed to incorporate these sequences into
      amplification products

<400> SEQUENCE: 11
ggatgctaat acgactcact atagggagaa gggccaccat ggactacaaa gacgatgacg    60

<210> SEQ ID NO 12
<211> LENGTH: 60
<212> TYPE: DNA
<213> ORGANISM: Artificial Sequence
<220> FEATURE:
<223> OTHER INFORMATION: complimentary sequence to SEQ ID 11 containing
      cohesive end to enhance directional ligation to a gene for
      amplification
<220> FEATURE:
<221> NAME/KEY: promoter
<222> LOCATION: (1)..(60)
<223> OTHER INFORMATION: complimentary sequence to SEQ ID 11 containing
      cohesive end to enhance directional ligation to a gene for
      amplification

<400> SEQUENCE: 12
cctacgatta tgctgagtga tatccctctt cccggtggta cctgatgttt ctgctactgc    60

<210> SEQ ID NO 13
<211> LENGTH: 50
<212> TYPE: DNA
<213> ORGANISM: Artificial Sequence
<220> FEATURE:
<223> OTHER INFORMATION: complimentary sequence to SEQ ID 14 containing
      a cohesive end to enhance directional ligation to a gene for
      amplification
<220> FEATURE:
<221> NAME/KEY: primer_bind
<222> LOCATION: (1)..(50)
<223> OTHER INFORMATION: complimentary sequence to SEQ ID 14 containing
      a cohesive end to enhance directional ligation to a gene for
      amplification
<400> SEQUENCE: 13
gatcttgaaa actaaccata cgtcatgtgc ccaccagcct tgtcctaata               50

<210> SEQ ID NO 14
<211> LENGTH: 46
<212> TYPE: DNA
<213> ORGANISM: Artificial Sequence
<220> FEATURE:
<223> OTHER INFORMATION: reverse primer containing a stop codon designed
      to incorporate these sequences into PCR amplification products
<220> FEATURE:
<221> NAME/KEY: primer_bind
<222> LOCATION: (1)..(46)
<223> OTHER INFORMATION: reverse primer containing a stop codon designed
      to incorporate these sequences into PCR amplification products
<400> SEQUENCE: 14 aactttgat tggtatgcag tacacgggtg gtcggaacag gattat                    46